United States Patent
Chen et al.

(10) Patent No.: US 10,149,782 B2
(45) Date of Patent: Dec. 11, 2018

(54) ORAL INTERFACE AND METHOD USING THE SAME

(71) Applicant: Somnics, Inc., Hsinchu (TW)

(72) Inventors: Chung-Chu Chen, Hsinchu (TW); Yin-Ruei Chen, Hsinchu (TW)

(73) Assignee: Somnics, Inc., Hsinchu (TW)

(*) Notice: Subject to any disclaimer, the term of this patent is extended or adjusted under 35 U.S.C. 154(b) by 8 days.

(21) Appl. No.: 13/958,159

(22) Filed: Aug. 2, 2013

(65) Prior Publication Data
US 2014/0034064 A1    Feb. 6, 2014

Related U.S. Application Data

(60) Provisional application No. 61/679,457, filed on Aug. 3, 2012.

(51) Int. Cl.
*A61F 5/56* (2006.01)
*A61M 16/00* (2006.01)
*A61M 16/04* (2006.01)

(52) U.S. Cl.
CPC .......... *A61F 5/566* (2013.01); *A61M 16/0057* (2013.01); *A61M 16/0493* (2014.02); *A61M 16/0495* (2014.02)

(58) Field of Classification Search
CPC .... A61F 5/56; A61F 5/566; A61F 2/00; A61F 2/20; A61F 2005/563; A61M 6/0057;
(Continued)

(56) References Cited

U.S. PATENT DOCUMENTS 2,937,445 A    5/1960  Erickson
4,169,473 A    10/1979 Samelson
(Continued)

FOREIGN PATENT DOCUMENTS

CN    101917924    12/2010
CN    102028574    4/2011
(Continued)

OTHER PUBLICATIONS

Chinese First Examination Communication with English translation for Application No. 201380041270.0, dated Oct. 10, 2015, 8 pages.
(Continued)

*Primary Examiner* — Victoria J Hicks
(74) *Attorney, Agent, or Firm* — Stinson Leonard Street LLP

(57) ABSTRACT

This invention provides an oral interface mainly including a connecting channel, a collapsible chamber and a non-collapsible structure disposed inside the collapsible chamber. The connecting channel communicates between the collapsible chamber and a negative source. When a negative pressure environment is generated inside the collapsible chamber via being pumped by the negative pressure source, the non-collapsible structure supports the collapsible chamber so that there are fluid channels formed inside the collapsible chamber. The air inside a user's oral cavity can be pumped out via the fluid channels and the connecting channel. A negative pressure environment is hence formed inside the user's oral cavity.

16 Claims, 18 Drawing Sheets

(58) Field of Classification Search
CPC .............. A61M 6/0493; A61M 6/0495; A61M 16/0493; A61M 16/0495; A61M 16/00; A61M 16/0488; A61M 16/049; A63B 71/085; A61C 7/08; A61C 7/04; A61C 7/043; Y10S 602/902
USPC .............. 128/848, 859, 861, 862; 433/91–96
See application file for complete search history.

(56) References Cited

U.S. PATENT DOCUMENTS

| | | | |
|---|---|---|---|
| 4,304,227 A | | 12/1981 | Samelson |
| 4,676,240 A | * | 6/1987 | Gardy ............................ 128/848 |
| 5,465,734 A | * | 11/1995 | Alvarez ................... A61F 5/566 |
| | | | 128/848 |
| 5,692,523 A | | 12/1997 | Croll et al. |
| 5,876,199 A | | 3/1999 | Bergersen |
| 5,957,133 A | | 9/1999 | Hart |
| 6,877,513 B2 | * | 4/2005 | Scarberry ................ A61F 5/566 |
| | | | 128/200.24 |
| 6,976,491 B2 | * | 12/2005 | D'Agosto ...................... 128/859 |
| 7,918,222 B2 | | 4/2011 | Chen |
| 8,261,748 B1 | * | 9/2012 | Goldberg ................. A61F 5/566 |
| | | | 128/200.26 |
| 2003/0208149 A1 | | 11/2003 | Coffey |
| 2005/0166928 A1 | | 8/2005 | Jiang |
| 2005/0217678 A1 | | 10/2005 | McCormick et al. |
| 2006/0096600 A1 | | 5/2006 | Witt et al. |
| 2007/0277818 A1 | | 12/2007 | Chen |
| 2009/0120446 A1 | | 5/2009 | Vaska et al. |
| 2009/0288660 A1 | * | 11/2009 | Chen .................... A61M 1/0023 |
| | | | 128/204.19 |
| 2011/0048431 A1 | | 3/2011 | Li |
| 2011/0073119 A1 | * | 3/2011 | Chen ........................ A61F 5/566 |
| | | | 128/848 |
| 2011/0100376 A1 | | 5/2011 | Rousseau |
| 2011/0180075 A1 | | 7/2011 | Chen et al. |
| 2011/0180076 A1 | * | 7/2011 | Hegde et al. ................. 128/848 |
| 2011/0192404 A1 | | 8/2011 | Chen |
| 2011/0220124 A1 | | 9/2011 | Vaska et al. |
| 2012/0017918 A1 | | 1/2012 | Huang et al. |
| 2014/0034064 A1 | | 2/2014 | Chen et al. |
| 2014/0041668 A1 | | 2/2014 | Chen et al. |

FOREIGN PATENT DOCUMENTS

| | | |
|---|---|---|
| FR | 2930138 | 10/2009 |
| JP | 2008-183388 A | 8/2008 |
| JP | 2008183388 | 8/2008 |
| KR | 20090102950 | 10/2009 |
| TW | 200744551 A | 12/2007 |
| TW | 201110950 A1 | 4/2011 |
| TW | 201125599 A1 | 8/2011 |

OTHER PUBLICATIONS

Taiwanese Office action with English translation for Application No. 1011128565 dated Mar. 2, 2015, 9 pages.
Taiwanese Notice of Allowance with English translation for Application No. 1011128565 dated Jul. 28, 2015, 4 pages.
Taiwanese Office action with English translation for Application No. 104128584 dated Dec. 28, 2015, 5 pages.
PCT International Preliminary Report on Patentability for Application No. PCT/CN2013/080735, dated Feb. 3, 2015, 23 pages.

* cited by examiner

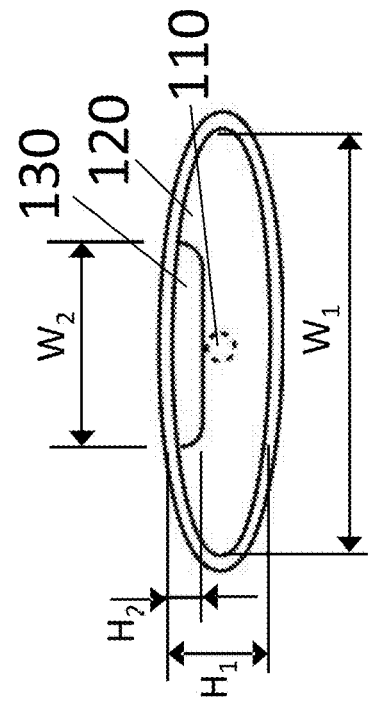
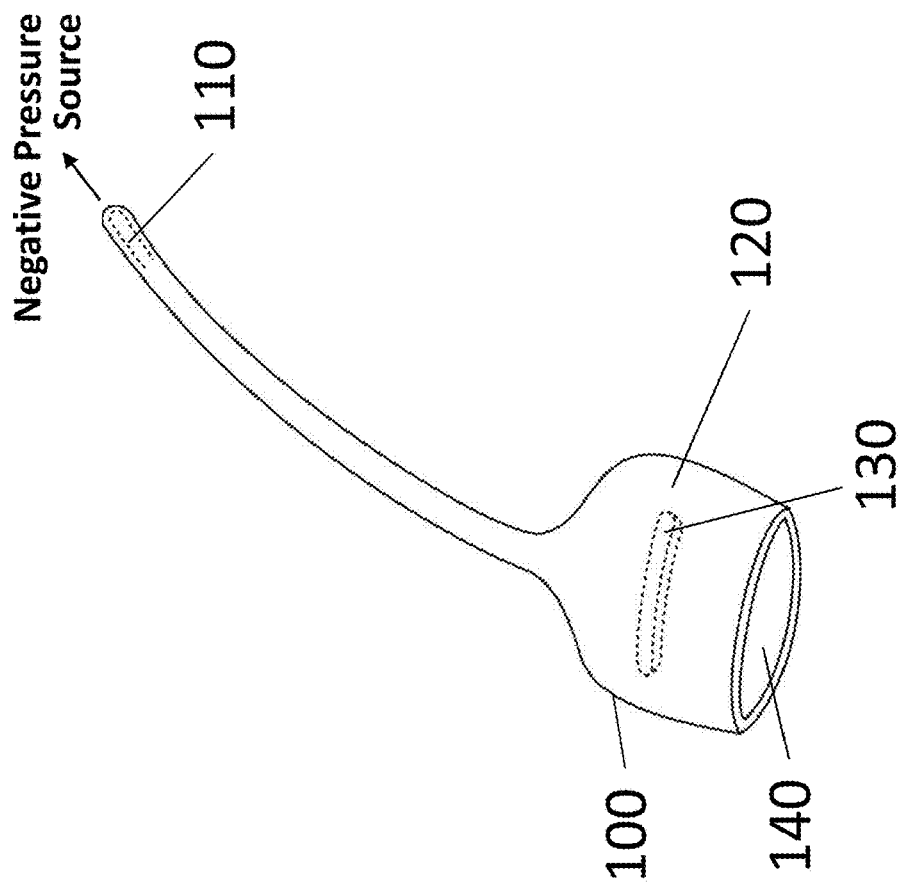
Figure 1A
Figure 1B

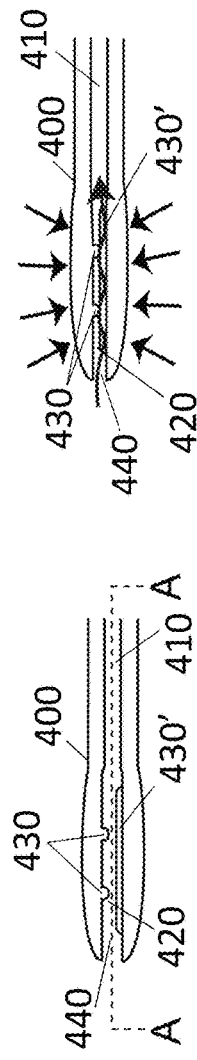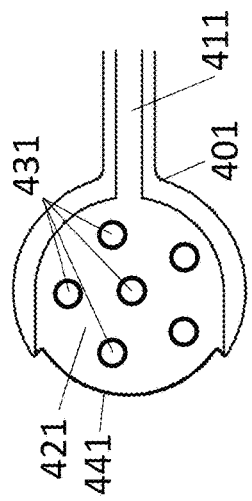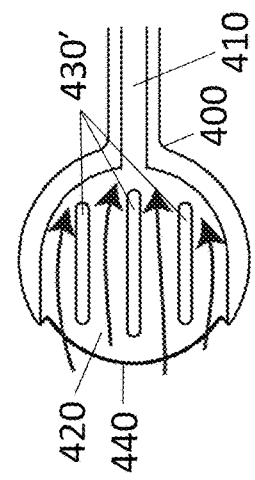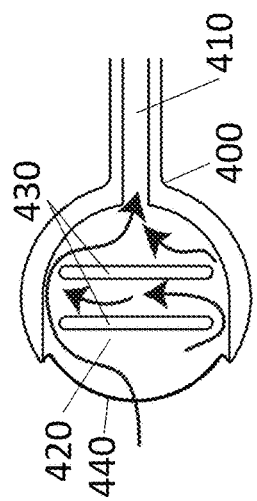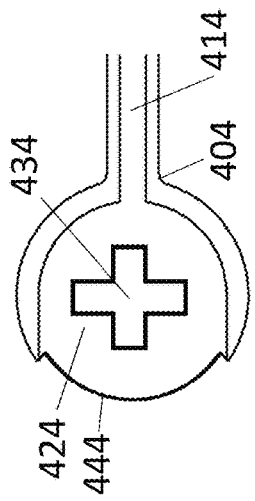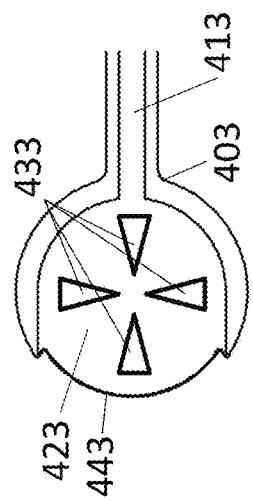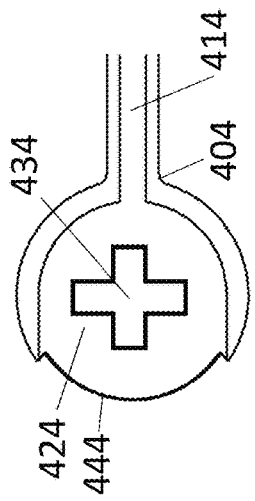

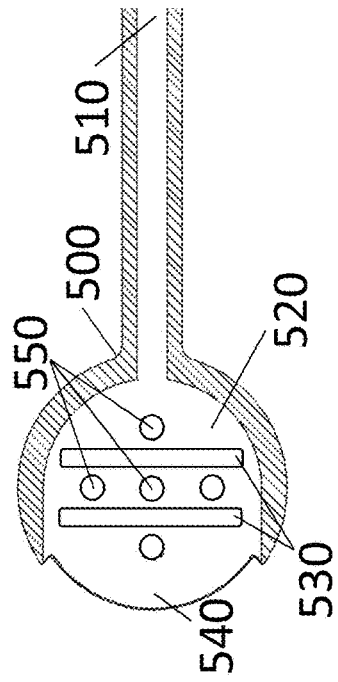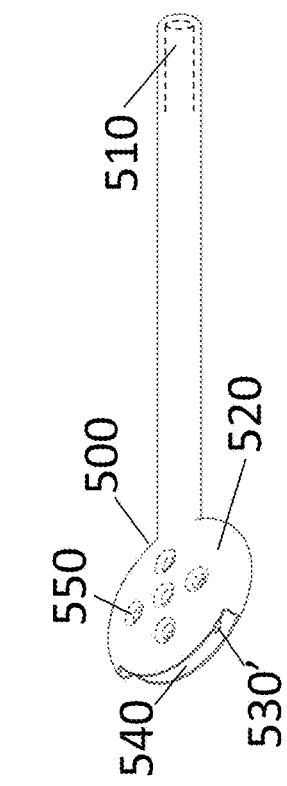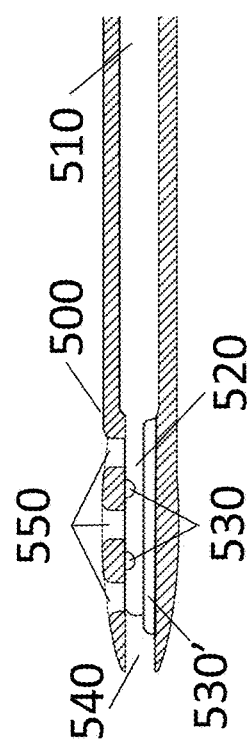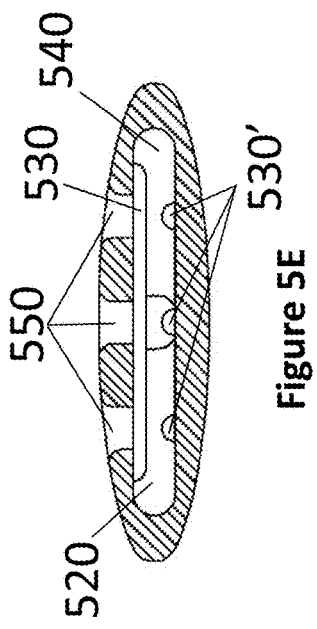
Figure 5A  Figure 5B  Figure 5C  Figure 5D  Figure 5E

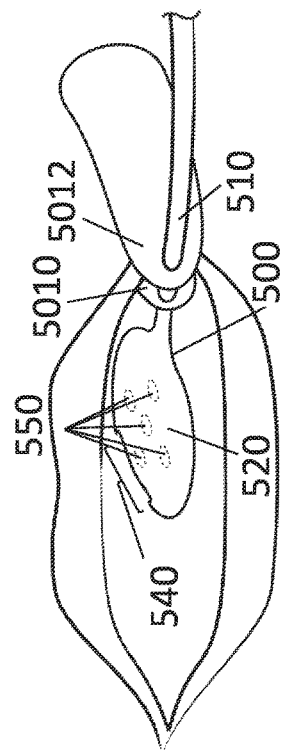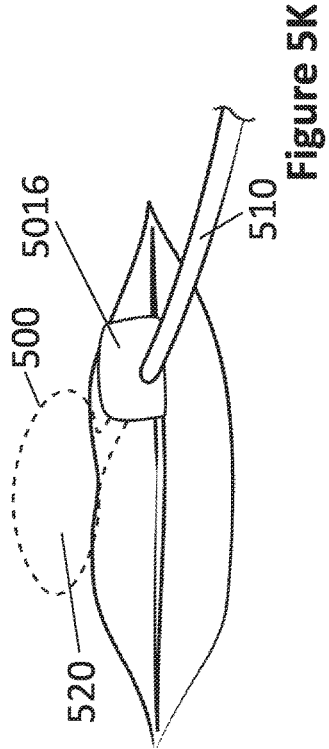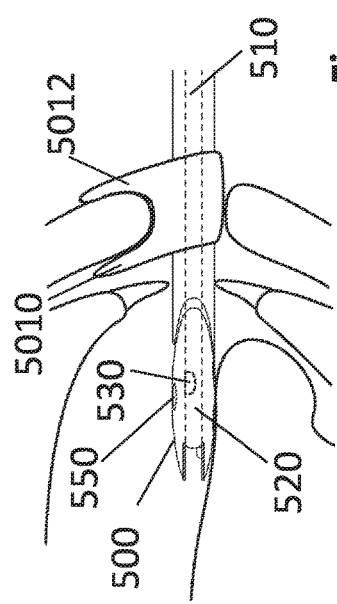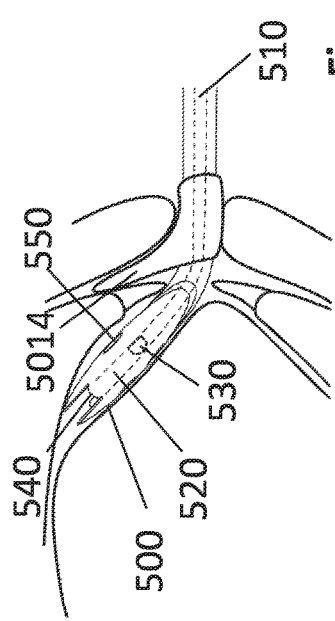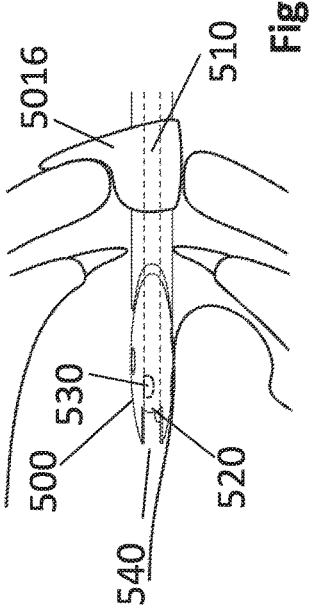

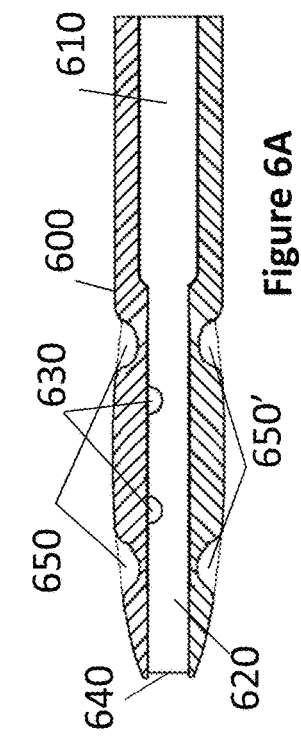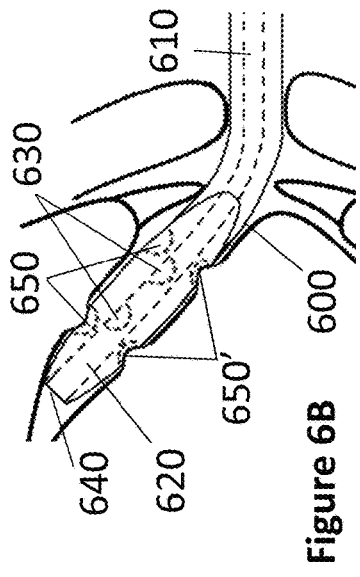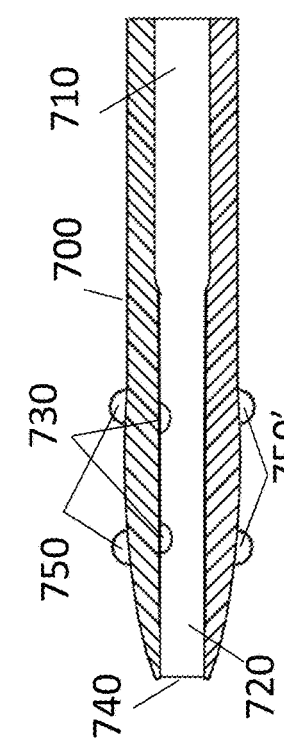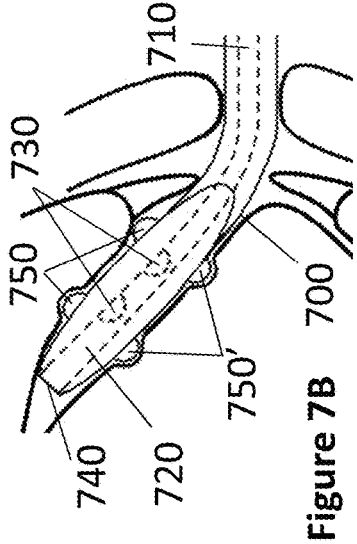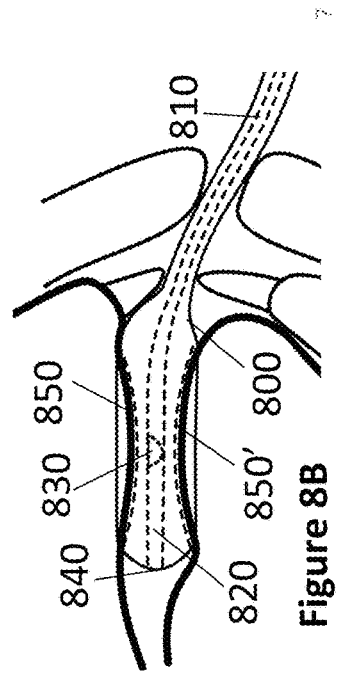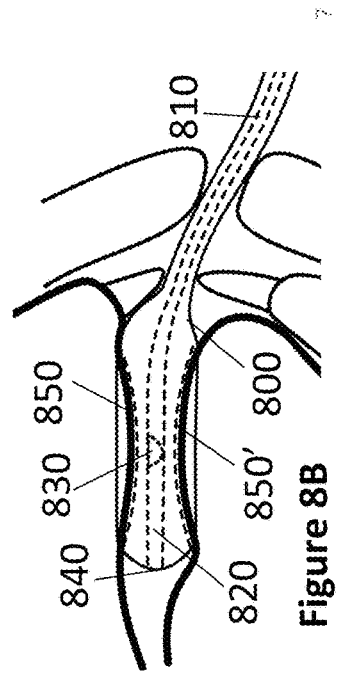

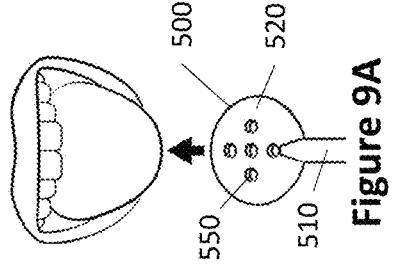

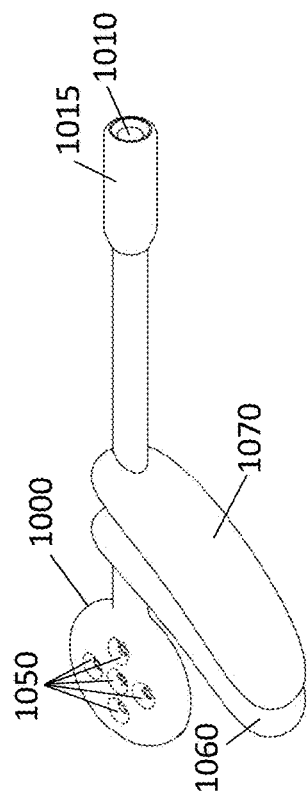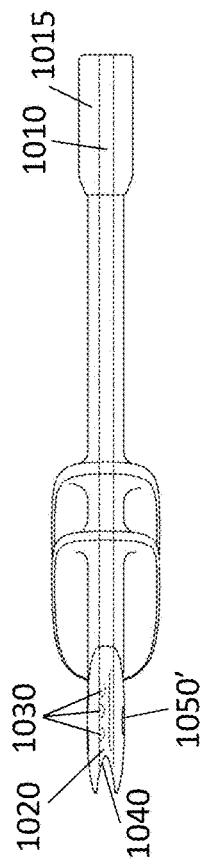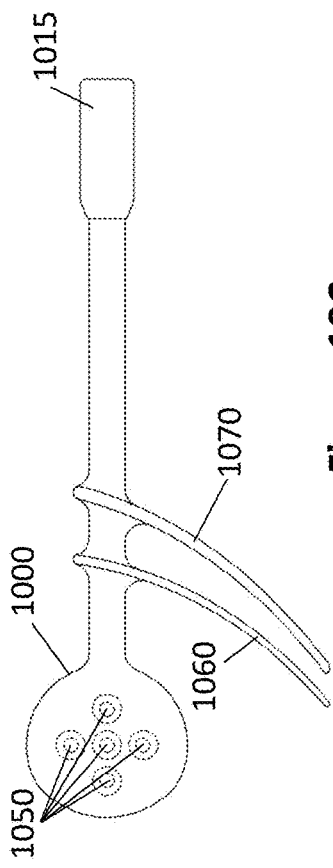
Figure 10A
Figure 10B
Figure 10C

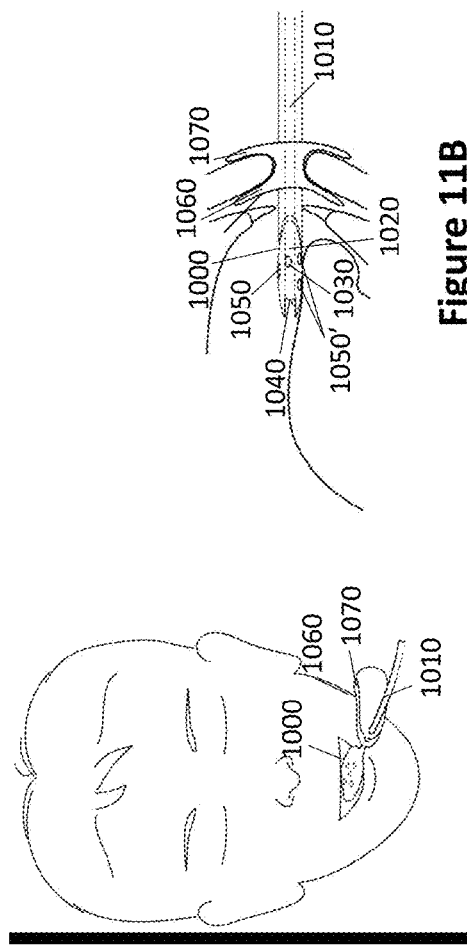
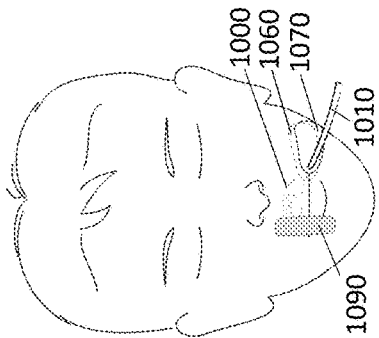
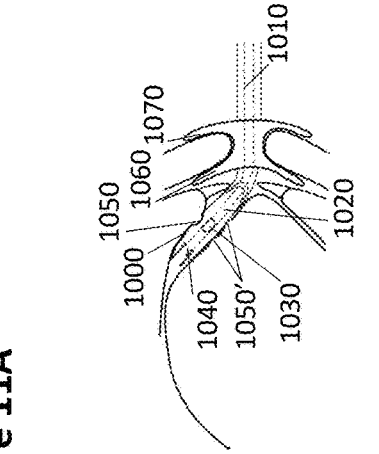
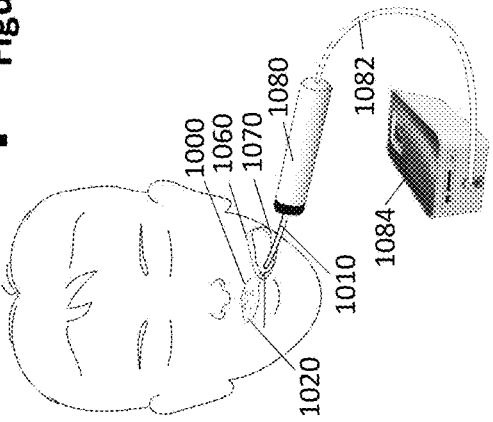

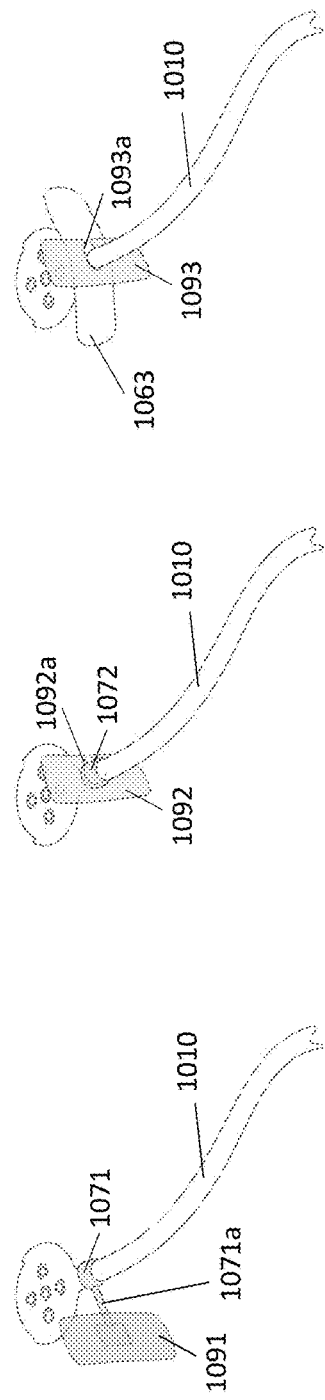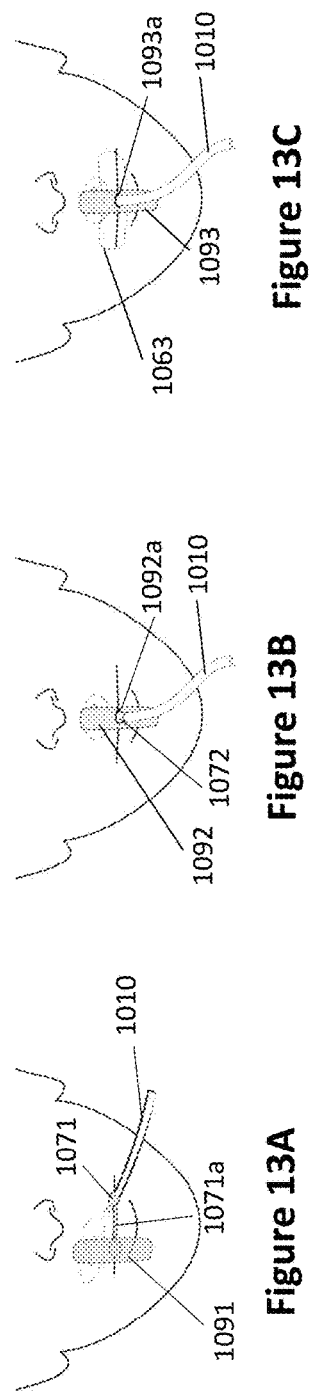

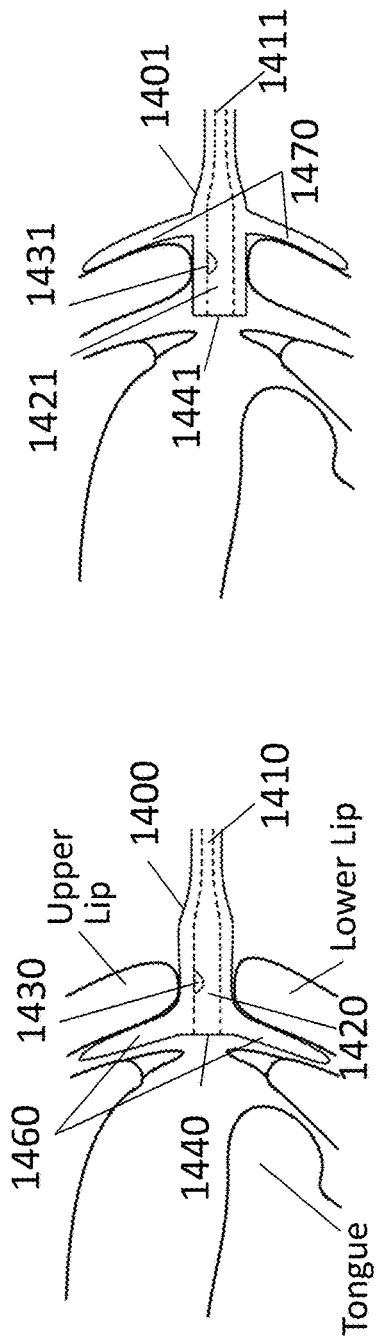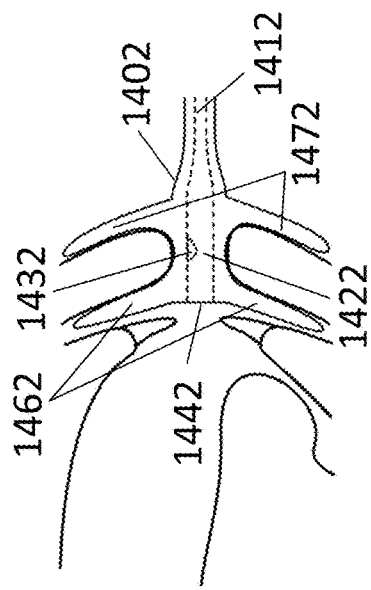
Figure 14A
Figure 14B
Figure 14C

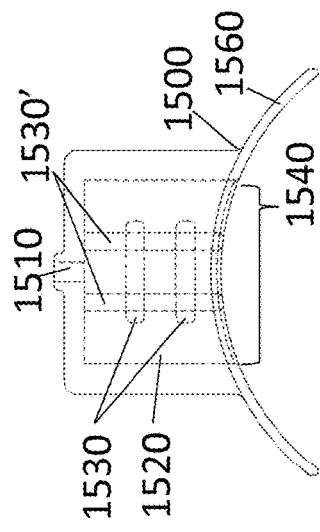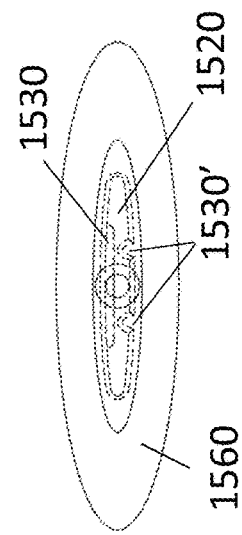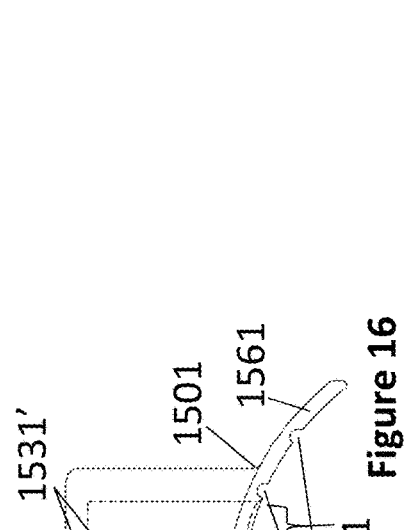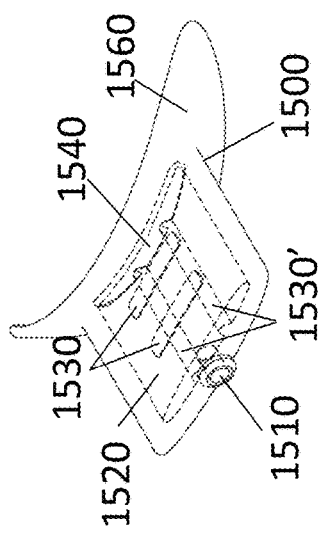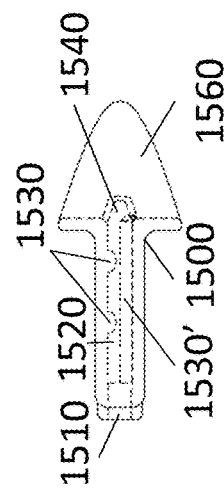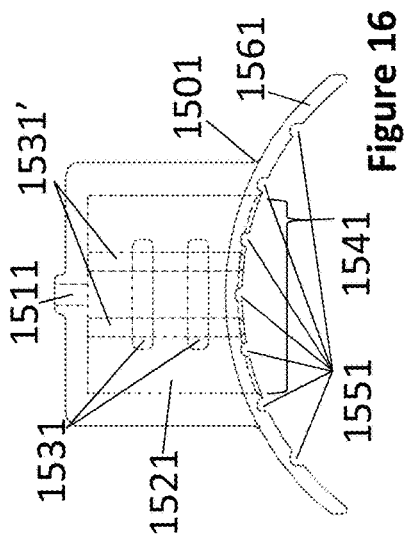
Figure 15A
Figure 15B
Figure 15C
Figure 15D
Figure 16

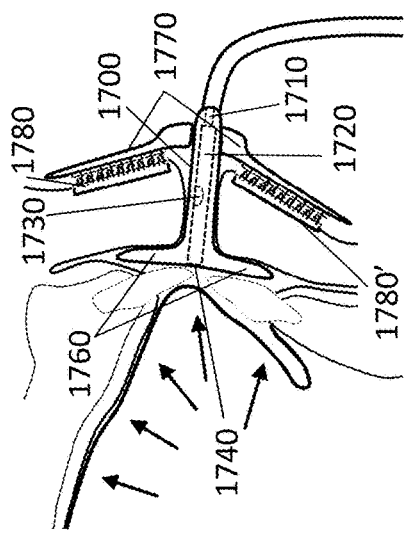
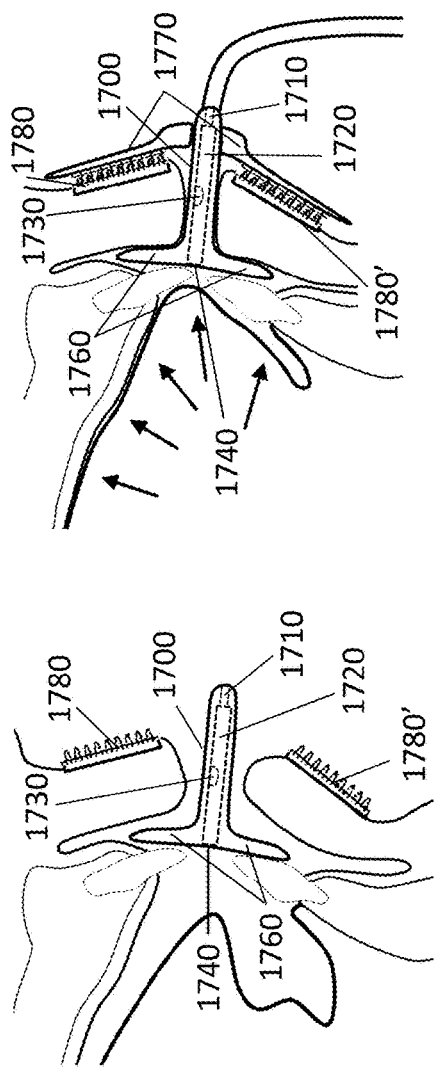
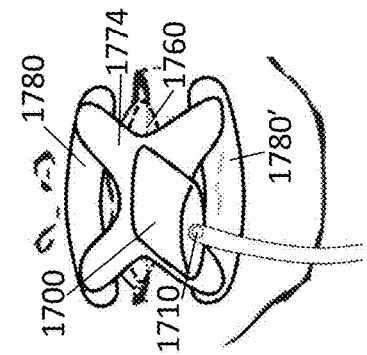
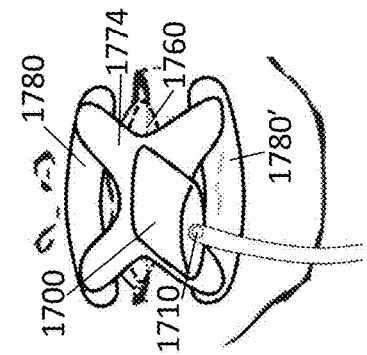
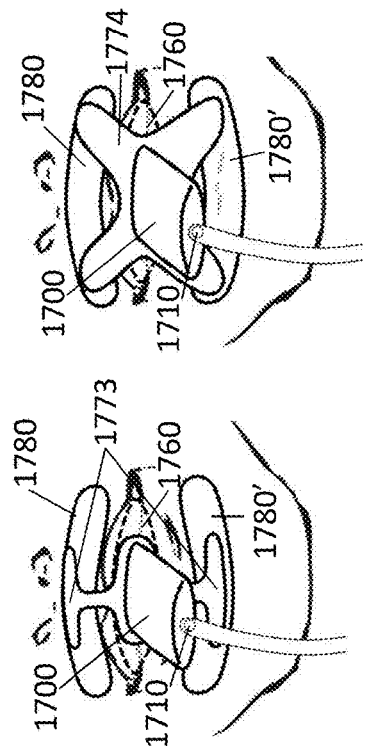
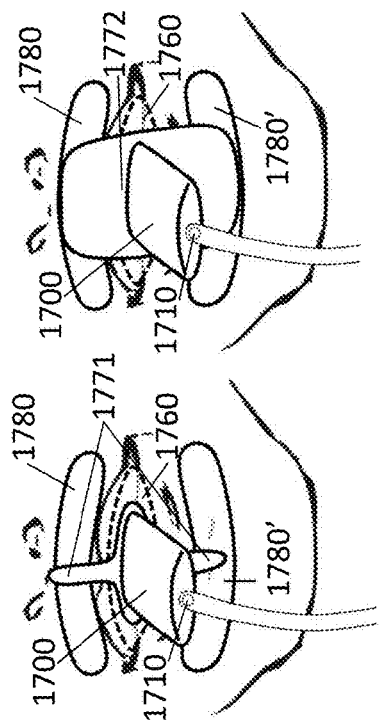

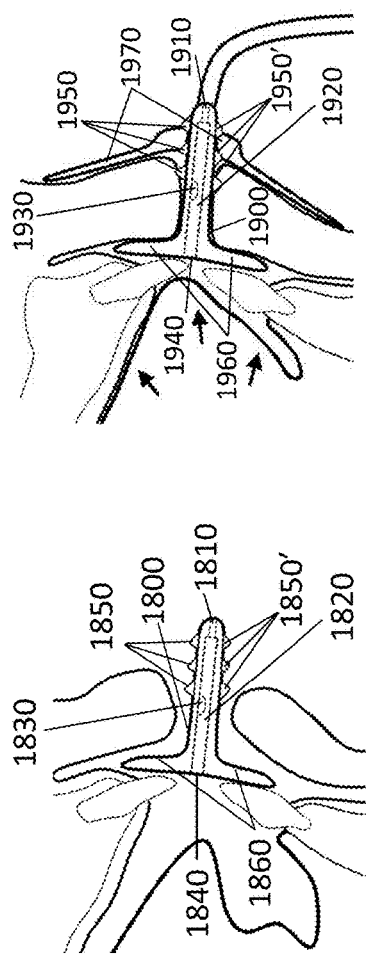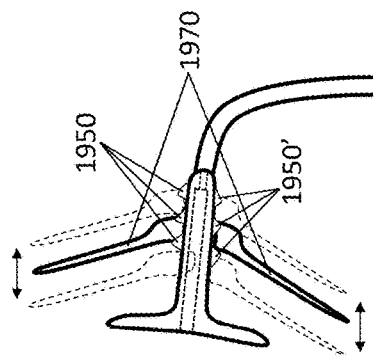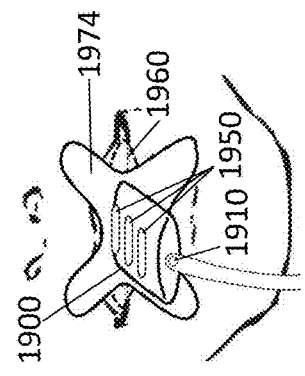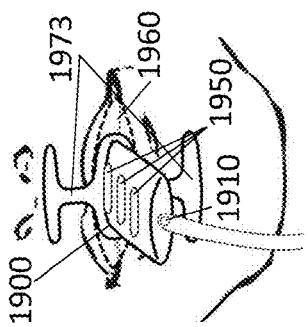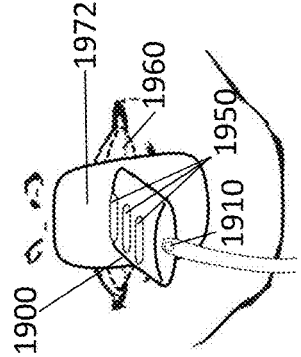

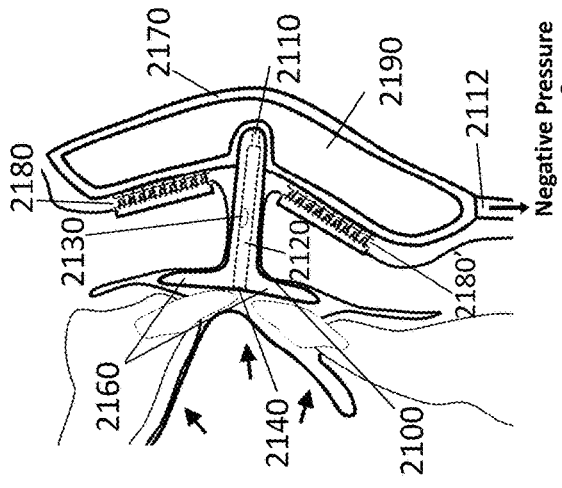
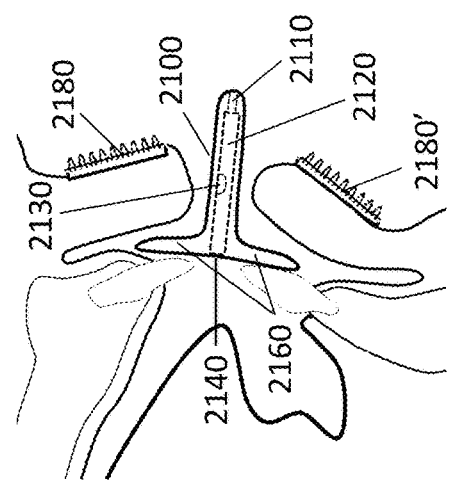
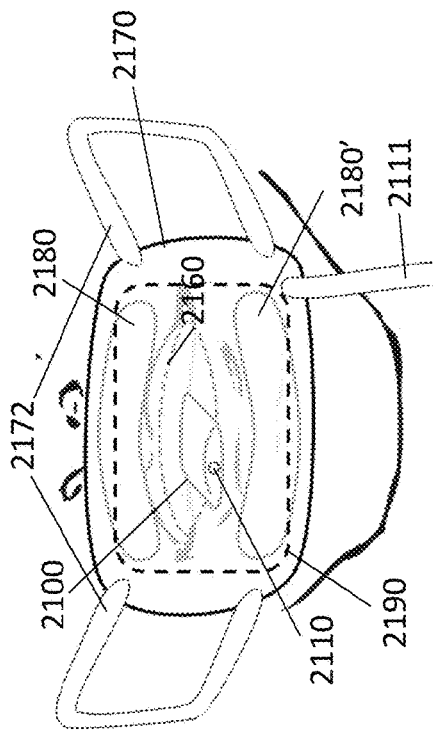
Figure 21A
Figure 21B
Figure 21C

US 10,149,782 B2

ORAL INTERFACE AND METHOD USING THE SAME

CROSS REFERENCE TO RELATED APPLICATIONS

This non-provisional application claims the benefit of U.S. Provisional Application No. 61/679,457 filed on Aug. 3, 2012. The entire contents of the above application are hereby incorporated by reference.

BACKGROUND OF THE INVENTION

Field of the Invention

The present invention relates to medical devices and methods that may prevent or reduce symptoms of obstructive sleep apnea (OSA). In particular, the present invention relates to a negative pressure oral interface device to be placed in the oral cavity of a patient.

Description of the Prior Art

Obstructive sleep apnea (OSA) is a condition in which repeated collapses in the patient's airway during inhalation causes a cessation of breathing during sleep. During inhalation, air pressure in the lungs and respiratory passages is reduced. If during this time, the tone of the muscles in the upper-airway is reduced, the airway tends to collapse. As the airway begins to occlude prior to an apnea episode, the patient often begins to snore. Snoring is an effort to try to combat the collapsed airway. These obstructions occur in different locations along the respiratory pathway in different patients, but the two common locations are the oropharynx or the nasopharynx.

People with moderate to severe OSA experience daytime sleepiness, fatigue, and poor concentration. In addition to these immediate problems, research has shown that patients with OSA use more medical resources, have an increased risk of medical disability, and finally have a higher mortality rate. Patients with severe OSA are estimated to have a three to six fold increased risk of mortality considering all causes. OSA is also implicated in many cardiovascular conditions, such as systemic hypertension and some degree of pulmonary hypertension. It is associated with an increased risk for myocardial infarction, cerebrovascular disease, and cardiac arrhythmia. OSA causes excessive daytime sleepiness due to interrupted sleeping pattern at night which leads to inability to concentrate. Patients' daily functions are impaired as their neuro-cognitive function is compromised. They are more likely to make errors and run into accidents. Therefore, OSA is a significant medical condition with serious negative outcomes if left untreated.

There are several current treatment options for OSA patients. Oral interfaces are used to treat mild OSA, but they often don't work well and cause damage to gums and teeth. Several types of surgery are used to treat OSA, however, surgical options are invasive, expensive and painful with recovery periods up to 6 months. The most common treatment for moderate to severe sleep apnea in adults is CPAP, which has 96% market share in OSA therapeutics. A CPAP machine consists of a mask, a pump and a humidifier. The device continuously blows pressurized air into the patient's nose to keep the airway open during sleep. CPAP is quite effective; however, it has unpleasant side effects such as dry throat and nose congestion. Patients who use CPAP often feel bloated in the morning and experience headaches. The machine is noisy and uncomfortable for the user and their partner. CPAP is currently the first-line and gold standard treatment, but it suffers low compliance due to significant side effects.

It has been proposed to apply a negative pressure to the patient's oral cavity to pull the tongue and soft palate forward to maintain the patency of the airway, as an improvement over CPAP, for example, U.S. Pat. No. 5,957,133, U.S. Patent and Patent Publication Nos. 2005/0166928, and 2006/0096600. While promising in theory, these prior arts comprise relatively large structures to engage the teeth and/or to retain the tongue. These approaches tend to occupy a lot of space in the oral cavity, which may cause discomfort and damage to large area of teeth, gum, and soft tissues. At the same time, the presence of such larger devices may induce excess saliva secretion and elicit the gag reflex. The other major disadvantage of these approaches is that the oral devices are anatomically dependent, requiring special technicians to customize the interface for each individual patient.

SUMMARY OF THE INVENTION

According to the above, an object of the present invention is to provide alternative and improved oral interface devices and methods of use for treatment of obstructive sleep apnea or snoring. Another object of the present invention is to provide small oral interface devices and methods to minimize the clear space within the oral cavity. Still another object of the present invention is to provide comfortable, convenient, and compact oral interface devices and methods of use that may be easy to implement and can effectively maintain the patient's airway patency during sleep.

The present invention provides oral interface devices and methods of use for reducing or treating snoring or obstructive sleep apnea by applying negative pressure in oral cavity via a small oral interface. The negative pressure pulls the tongue toward the upper palate and pulls the soft palate forward. By moving both the tongue and the soft palate forward, the airway patency near the oropharynx can be maintained to prevent disordered breathing during sleep. The negative pressure also pull the lips inward to close the mouth, thus preventing air from the outside entering the oral cavity. The negative pressure further pulls the soft palate toward the rear surface of the tongue to create a closed area to prevent air entering the oral cavity through the nasal passages.

The present invention provides an oral interface device which comprises a connecting tube with one end connecting to a negative pressure source, a collapsible chamber having upper and lower walls and first and second open longitudinal ends, the upper and lower walls each having an exterior surface and an interior surface, wherein the first longitudinal end of the collapsible chamber is fluidly connected to the second longitudinal end of the connecting tube, and non-collapsible structures disposed between the interior surfaces of the upper and lower walls of the collapsible chamber. The non-collapsible structures having lengths extending longitudinally along the collapsible chamber and are spaced apart from one another such that the interior surfaces of the upper and lower walls of the collapsible chamber and the non-collapsible structures define a fluid channel extending longitudinally along the collapsible chamber. The fluid channel fluidly connects the second open longitudinal end of the collapsible chamber and the second longitudinal end of the connecting tube. Further aspects of the present invention include an oral interface device where the non-collapsible structures are disposed between the upper and lower walls of the collapsible chamber, the non-collapsible structures being spaced longitudinally inward from the second open longitudinal end of the collapsible chamber and spaced longitudinally inward from the first open longitudinal end of the collapsible chamber, and the non-collapsible structures being disposed inward of side edges of the upper and lower walls of the collapsible chamber. When a negative pressure environment is generated by the negative pressure source in the collapsible chamber, soft tissue in the oral cavity leans upon the collapsible chamber, then compresses and collapses the collapsible chamber. The non-collapsible structure supports the collapsible chamber and maintains internal fluid passages inside the collapsible chamber in a collapsed condition, thus keeps fluid communication between the oral cavity and the negative pressure source. When the tissue in the oral cavity is moved by a patient or involuntarily, the collapsible chamber may resume its original volume. The resuming process of the collapsible chamber causes self-generated vacuum effect due to increasing volume, which increases the force to pull back the tissue or to prevent the tissue from movement.

In another aspect, the present invention provides methods to generate negative pressure in a user's oral cavity in order to stabilize oral soft tissue. The method can employ the above-mentioned or other oral interface devices to achieve similar effect in stabilizing oral soft tissues. The method comprises the following steps: placing an oral interface device in the oral cavity and positioning a collapsible chamber of the oral interface device at anterior portion (a half or a third) of a tongue and middle region of the upper dental arch; extending a connecting tube of the oral interface device connected to the collapsible chamber from the mouth to negative pressure source outside of the oral cavity; adjusting the connecting tube of the oral interface device to a proper position, preferably moving the connecting tube to one of the biting opening of canine teeth; activating the negative pressure source with the lips closed tightly. Air within the user's oral cavity is evacuated via the internal fluid passages inside the collapsible chamber and the connecting tube. A negative pressure environment is maintained in the use's oral cavity, and at the same time, soft tissues in the oral cavity lean on the collapsible chamber, compress, and collapse the collapsible chamber, therefore, to minimize the clear space or space occupied by the oral interface device within the oral cavity.

Additionally, the oral interface device may be placed at one of the following places: a location between the user's tongue and hard palate, a location between the user's tongue and lower jaw, a location between teeth and lips, a location between an outside surface of teeth and a lateral wall inside the oral cavity, or a location between the user's tongue and soft palate.

Methods of the present invention may further contain, using a non-collapsible structure to support the collapsible chamber, so that the collapsible chamber can preserve internal fluid passages after being collapsed, in order to keep the negative pressure source connected to the oral cavity. Methods of the present invention may still further contain, using a gripping structure on one external wall of the collapsible chamber, so that the gripping structure can press up against and grip the soft tissues in the user's oral cavity after the collapsible chamber being collapsed, in order to stabilize soft tissues. Methods of the present invention may still further contain, using an adhesive patch to attach to the user's lips, in order to prevent users from involuntary opening his mouth, thus maintaining oral negative pressure environment.

The above-mentioned devices and methods require only partial evacuation time of the negative pressure source, which are more energy-saving and quieter. The oral interface devices of the present invention are also more compliant to the shape of the oral tissues, more comfortable, and taking less space inside the mouth.

BRIEF DESCRIPTION OF THE DRAWINGS

FIGS. 1A and 1B illustrate perspective and front views, respectively, of an oral interface according to a first embodiment of the present invention;

FIG. 4A illustrates a cross-sectional view without negative pressure applied and FIGS. 4B to 4D illustrate cross-sectional, top, and bottom view, respectively, with negative pressure applied of a variation of oral interfaces according to the first embodiment of the present invention;

FIGS. 4E to 4H illustrate top views of variations of the oral interface according to the first embodiment of the present invention;

FIGS. 5A to 5E illustrate perspective, top-, side-, bottom-, and front-cross-sectional views, respectively, of an oral interface according to a second embodiment of the present invention;

FIGS. 5F to 5K illustrate cross-sectional and front views of variations of the oral interface according to the second embodiment of the present invention;

FIG. 6A illustrates a cross-sectional view of another variation of the oral interface according to the second embodiment of the present invention and FIG. 6B illustrates placement of the oral interface in the user's oral cavity with negative pressure applied;

FIG. 7A illustrates a cross-sectional view of yet another variation of the oral interface according to the second embodiment of the present invention and FIG. 7B illustrates placement of the oral interface in the user's oral cavity with negative pressure applied;

FIG. 8A illustrates a cross-sectional view of still another variation of the oral interface according to the second embodiment of the present invention and FIG. 8B illustrates placement of the oral interface in the user's oral cavity with negative pressure applied;

FIGS. 9A to 9I illustrate application diagrams and a method of applying the oral interface according to the second embodiment of the present invention and FIG. 9J illustrates a cross-sectional view of the oral interface in the user's oral cavity with negative pressure applied;

FIGS. 10A to 10C illustrate perspective, side, and top views, respectively, of an oral interface according to a third embodiment of the present invention;

FIGS. 11A to 11E illustrate application diagrams and a method of applying the oral interface according to the third embodiment of the present invention;

FIGS. 12A to 12C illustrate perspective views of variations of the oral interface according to the third embodiment of the present invention;

FIGS. 13A to 13C illustrate front views of the oral interface according to the third embodiment after placement in the oral cavity;

FIG. 14A illustrates a cross-sectional view of an oral interface according to a fourth embodiment of the present invention;

FIG. 14B illustrates a cross-sectional view of an oral interface according to a fifth embodiment of the present invention;

FIG. 14C illustrates a cross-sectional view of an oral interface according to a sixth embodiment of the present invention;

FIGS. 15A to 15D illustrate perspective, top, side, and front views, respectively, of a variation of the oral interface according to the fourth embodiment of the present invention;

FIG. 16 illustrate a top view of another variation of the oral interface according to the fourth embodiment of the present invention;

FIGS. 17A to 17F illustrate variations of the oral interface according to the sixth embodiment of the present invention;

FIG. 18 illustrates a side view of an oral interface according to a seventh embodiment of the present invention;

FIG. 19A illustrates a side view of an oral interface according to an eighth embodiment of the present invention and FIG. 19B illustrates placement of the oral interface in the user's oral cavity with negative pressure applied;

FIGS. 20A to 20D illustrate variations of the oral interface according to the eighth embodiment of the present invention;

FIGS. 21A to 21C illustrate partial cross-sectional view, cross-sectional view with negative pressure applied, and front view of an oral interface according to a ninth embodiment of the present invention;

DETAILED DESCRIPTION OF THE PREFERRED EMBODIMENTS

Figure 2A:
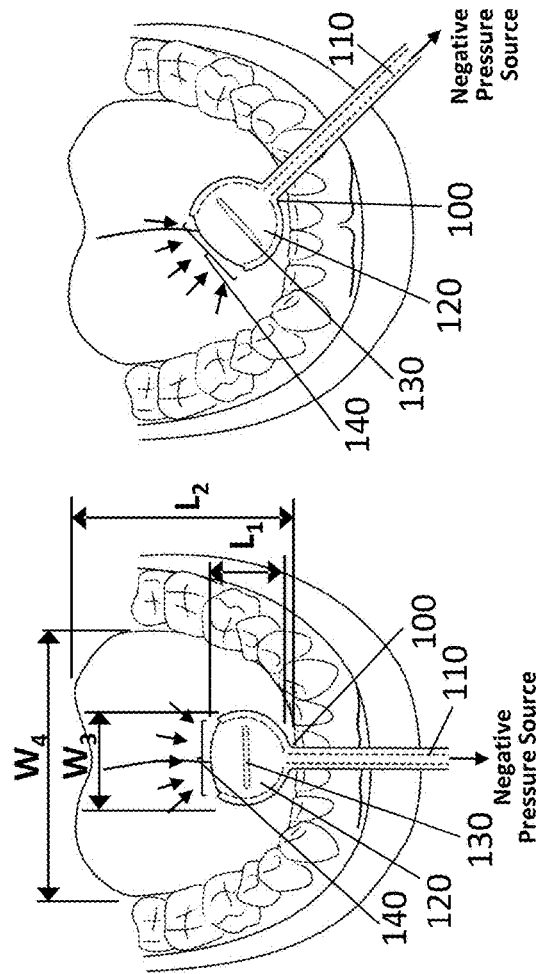
FIGS. 2A to 2E illustrate application diagrams of the oral interface according to the first embodiment of the present invention.

The object, spirit, and advantages of the preferred embodiments of the present invention will be readily understood by the accompanying detailed descriptions and drawings.

FIGS. 1A and 1B show perspective and front views, respectively, of an oral interface device according to the first embodiment of the present invention. In the first embodiment, an oral interface 100 comprises a connecting tube 110, with one end connecting to a negative pressure source (not shown); a collapsible chamber 120, with one end connecting to the other end of the connecting tube 110 in relative to the negative pressure source; an open end 140 on another end of the collapsible chamber 120; a non-collapsible structure 130, for example, comprising a rib, disposed on at least one internal wall of the collapsible chamber 120. Referring to FIG. 1B, the non-collapsible structure 130 has a width $W_2$ smaller than an internal width $W_1$ of the collapsible chamber 120. The non-collapsible structure 130 has a height $H_2$ smaller than an internal height $H_1$ of the collapsible chamber 120.

Figure 2B:
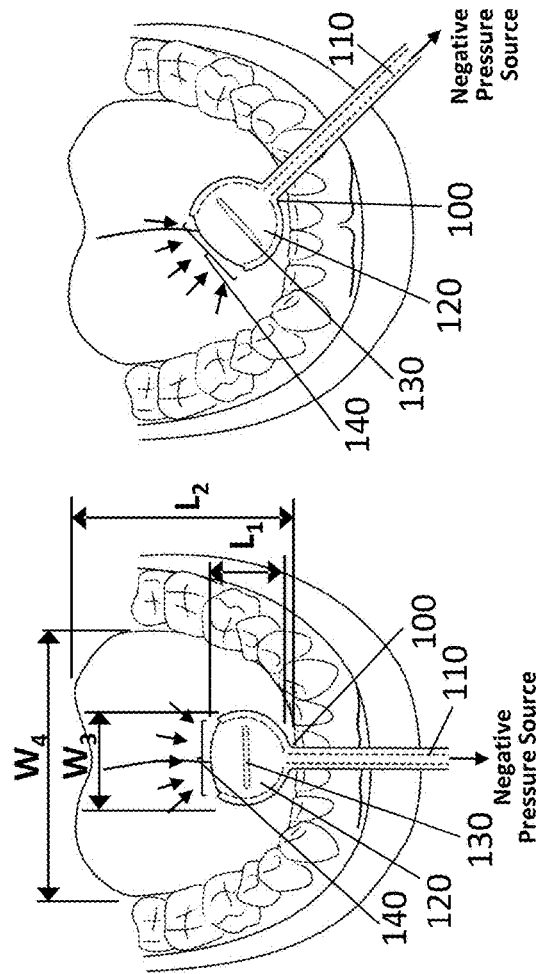
Figure 2C:
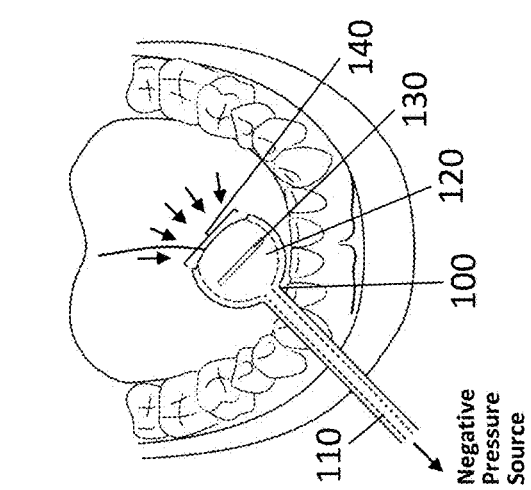
Figure 2D:
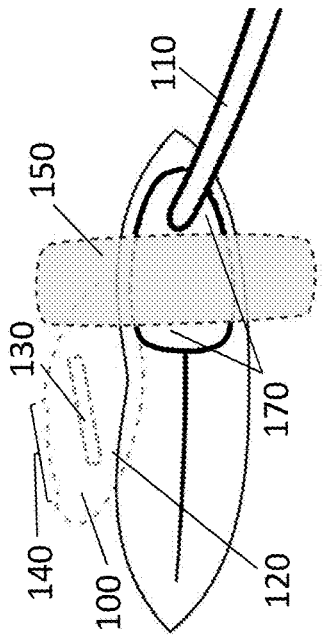
Figure 2E:
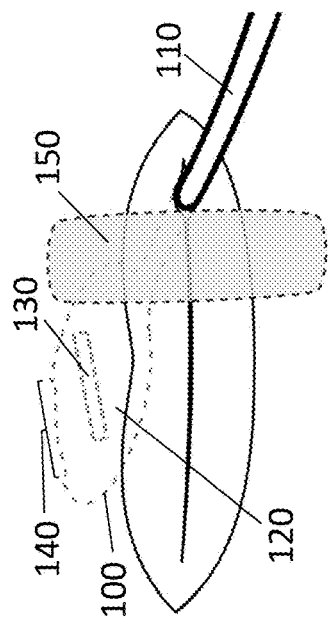

FIG. 2A to FIG. 2E show different views of the oral interface 100 in use. Referring to FIGS. 2A to 2C, the collapsible chamber 120 of the oral interface 100 is placed at anterior region (a half or a third) of the tongue and middle region of the upper dental arch. The position and orientation of the oral interface 100 can be adjusted properly, for example, the connecting tube 110 can be moved its position to the biting positioning of the left or right canine teeth, as shown in FIGS. 2A and 2C, or the connecting tube 110 can be moved to the front teeth. Referring to FIG. 2B, the collapsible chamber 120 has an external width $W_3$ smaller than the width $W_4$ of the user's dental arch. Moreover, as shown in FIG. 2B, the collapsible chamber 120 of the oral interface 100 can be placed at anterior one half portion of the tongue, or preferably, anterior one third portion of the tongue. Therefore, the collapsible chamber 120 has an external length $L_1$ smaller than one half of the tongue length $L_2$, or preferably, smaller than one third of the tongue length $L_2$. Besides, as shown in FIG. 2D, the connecting tube 110 is moved to the biting position of the canine teeth, after the user closes the mouth, an adhesive patch 150 can be further attached to a proper position near the user's lips, for example, the corner of the mouth, to prevent the user from opening the mouth involuntarily, thus avoiding the oral interface 100 dropping out of the mouth. Besides, as shown in FIG. 2E, the oral interface 100 can further comprise an external shield member 170, disposed between the collapsible chamber 120 and the connecting tube 110. During usage of the oral interface 100, the external shield member 170 can be attached to the user's mouth, in order to facilitate positioning and to limit moving of the oral interface 100 within the oral cavity, thus avoiding the oral interface 100 being swallowed or dropping out. Furthermore, the adhesive patch 150 can be attached to the external shield member 170 and upper and lower portion of the user's mouth.

Figure 3B:
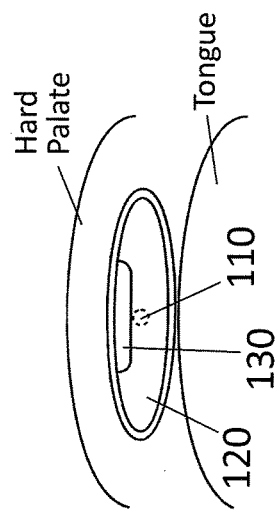
FIGS. 3A and 3B illustrate cross-sectional and front views, respectively, of the oral interface placed in an oral cavity without negative pressure applied according to the first embodiment of the present invention.
Figure 3D:
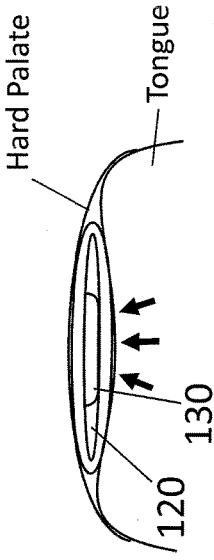
FIGS. 3C and 3D illustrate cross-sectional and front views, respectively, of the oral interface placed in an oral cavity with negative pressure applied according to the first embodiment of the present invention.
Figure 3E:
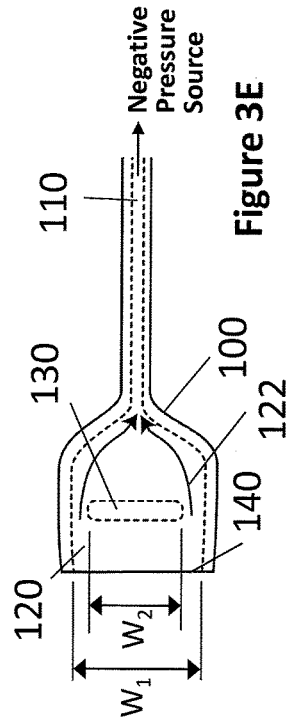
FIG. 3E illustrates top view of the oral interface with negative pressure applied according to the first embodiment of the present invention.
Figure 3A:
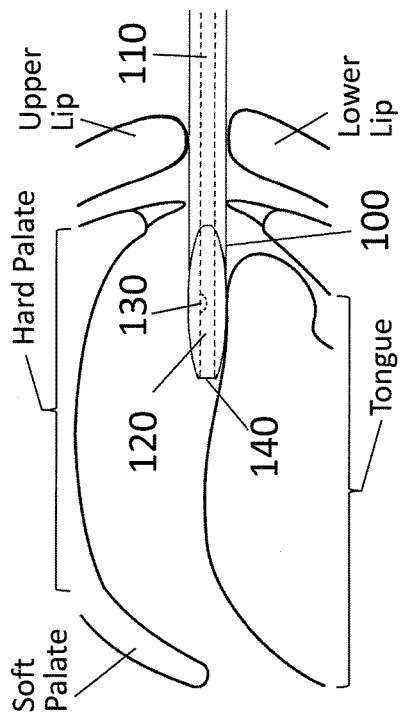
Figure 3C:
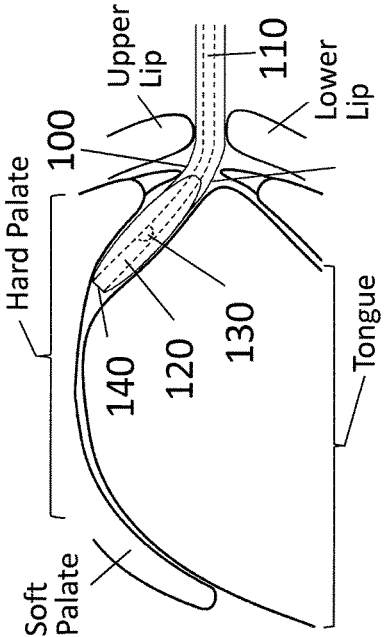

FIGS. 3A and 3B show cross-sectional and front views of the oral interface 100 placed at the positions in user's oral cavity as shown in FIGS. 2A to 2C without the negative pressure source activated, wherein large clear space with air resides between tongue and upper palate. FIGS. 3C and 3D show cross-sectional and front views of the oral interface 100 with the negative pressure source activated, wherein the air in the oral cavity is evacuated through the collapsible chamber 120 of the oral interface 100 to form a negative pressure environment. Soft tissue in the oral cavity leans upon the collapsible chamber 120, then compresses and collapses the collapsible chamber 120, as shown in FIG. 3E. The collapsible chamber 120 can have deformability, which is not only compliant to the shape of intraoral tissues such as the hard palate or the tongue, but also occupies less intraoral space and provides better comfortableness. The non-collapsible structure 130 can support the collapsible chamber 120 and maintain internal fluid passages inside the collapsible chamber 120 in a collapsed condition in the negative pressure environment, thus keeps fluid communication via fluid channels 122 between the oral cavity and the negative pressure source, as shown in FIG. 3E. When the tissue in the oral cavity is moved by a patient or involuntarily, the compressed collapsible chamber 120 may resume its original volume. The resuming process of the collapsible chamber 120 causes self-generated vacuum effect due to increasing volume, which increases the negative pressure and forces to pull back the tissue or to prevent the tissue from movement, as shown in FIG. 3D. The open end 140 of the collapsible chamber 120 provides fluidic communication of the oral cavity to the negative pressure source via the internal fluid passages of the collapsible chamber 120 and the connecting tube 110. The negative pressure source evacuates air from the oral cavity, creates a negative pressure environment, and pulls the tongue, the soft palate and other soft tissues forward to maintain airway patency.

FIG. 4 shows variations of the first embodiment of the present invention. FIG. 4A shows a cross-sectional view of the first variation without negative pressure applied. FIGS. 4B to 4D illustrate cross-sectional, top, and bottom view, respectively, of the first variation with negative pressure applied. The first variation of the present invention, an oral interface 400, has a non-collapsible structure different from the oral interface 100. The oral interface 400 has other equivalent parts the same as oral interface 100, for example, an open end 440, a connecting tube 410, and a collapsible chamber 420, etc., thus descriptions of which will not be repeated here. The oral interface 400 has a non-collapsible structure, which comprises a plurality of first ribs 430 and a plurality of second ribs 430'. Each individual of the first ribs 430 can be parallel to each other and spaced apart on an internal wall of the collapsible chamber 420. Each individual of the second ribs 430' can be parallel to each other and spaced apart on another internal wall, in relative to the first ribs 430, of the collapsible chamber 420. Besides, the first ribs 430 and the second ribs 430' can have a perpendicular or non-parallel stack configuration, as shown in FIGS. 4A to 4D. The non-collapsible structures of the present invention can be other non-rib protruding structures on the internal walls of the collapsible chamber, as shown in other variations of the first embodiment in FIGS. 4E to 4H. The other variations of the present invention, the oral interface 401, 402, 403, or 404, have a non-collapsible structure different from the oral interface 400 and the same other equivalent parts, for example, open ends 441, 442, 443, or 444, connecting tubes 411, 412, 413, or 414, and a collapsible chamber 421, 422, 423, or 424, etc., thus descriptions of which will not be repeated here. The second variation, as shown in FIG. 4E, has a non-collapsible structure 431 with circular protruding members on the internal wall of the collapsible chamber 421. The third variation, as shown in FIG. 4F, has a non-collapsible structure 432 with square protruding members on the internal wall of the collapsible chamber 422. The fourth variation, as shown in FIG. 4G, has a non-collapsible structure 433 with triangular protruding members on the internal wall of the collapsible chamber 423. The fifth variation, as shown in FIG. 4H, has a non-collapsible structure 434 with cross-shaped protruding members on the internal wall of the collapsible chamber 424. The second to fifth variations, the oral interface 401, 402, 403, or 404, of the first embodiment of the present invention have symmetrical or non-symmetrical non-collapsible structure 431', 432', 433', or 434' (not shown) on another internal wall of the collapsible chambers 421, 422, 423, or 424 in relative to the non-collapsible structure 431, 432, 433, or 434. The non-collapsible structures can support the collapsible chambers 421, 422, 423, or 424 when they collapsed in the negative pressure environment and maintain the internal flow passages within. The non-collapsible structures of the present invention can be any combination of the following different non-rib extruding structures' singular or plural permutations: circular, polygonal, cross-shaped or irregular-shaped.

FIG. 5 shows the oral interface device according to the second embodiment of the present invention. FIGS. 5A to 5E are the perspective, top cross-sectional, side cross-sectional, bottom cross-sectional, and front cross-sectional views, respectively, of the second embodiment. According to the second embodiment, an oral interface 500 of the present invention comprises a connecting tube 510 with one end connected to a negative pressure source (not shown), a collapsible chamber 520 with one end connecting to the connecting tube 510 in relative to the negative pressure, an open end 540 on another end of the collapsible chamber 520, a non-collapsible structure 530 and 530' on two opposite internal walls of the collapsible chamber 520, a first gripping structure 550 and a second gripping structure 550' disposed on the two opposite external walls of the collapsible chamber 520. The non-collapsible structures, 530 and 530', comprise a plurality of first ribs 530 and a plurality of second ribs 530'. Each individual of the first ribs 530 can be parallel to each other and spaced apart on an internal wall of the collapsible chamber 520. Each individual of the second ribs 530' can be parallel to each other and spaced apart on another internal wall, in relative to the first ribs 530, of the collapsible chamber 520. Besides, the first ribs 530 and the second ribs 530' can have a perpendicular or non-parallel stack configuration. The first gripping structure 550 can comprise a plurality of concave holes on the top external wall of the collapsible chamber 520, as shown in FIG. 5B. The second gripping structure 550' can comprise a plurality of concave holes on the bottom external wall of the collapsible chamber 520, as shown in FIG. 5D. When the oral interface 500 is placed in a user's mouth and creates a negative pressure environment in the oral cavity by the negative pressure source, the first gripping structure 550 and the second gripping structure 550' can grip the soft tissue within the user's oral cavity to facilitate positioning of the collapsible chamber 520. The oral interface 500 of the present invention can only have single side of the gripping structure 550 disposed on one external wall of the collapsible chamber 520. When the oral interface 500 is placed in a user's mouth and creates a negative pressure environment in the oral cavity by the negative pressure source, the gripping structure 550 can grip the soft tissue within the user's oral cavity to facilitate positioning of the collapsible chamber 520. The gripping structure 550 comprises plural concave holes can further be through-hole and connecting with the collapsible chamber 520. The concave holes can distribute negative pressure from the negative pressure sources and the connecting tube 510 and increase forces of the gripping structure 550 to grip soft tissues in the oral cavity in order to positioning of the collapsible chamber 520.

FIG. 5F to FIG. 5K show different variations of the oral interface device according to the second embodiment of the present invention. FIGS. 5F and 5G show cross-sectional and front views, respectively, of the first variation of the oral interface device placed in a user's oral cavity. FIGS. 5F and 5G show cross-sectional and front views, respectively, of the second variation of the oral interface device placed in a user's oral cavity. FIGS. 5H and 5I show cross-sectional and front views, respectively, of the second variation of the oral interface device placed in a user's oral cavity. FIGS. 5J and 5K show cross-sectional and front views, respectively, of the third variation of the oral interface device placed in a user's oral cavity. The difference between the first variation and the second embodiment of the oral interface device is that the oral interface device has an internal shield member 5010 and an external shield member 5012. The internal and external shield members, 5010 and 5012, can limit movement of the oral interface 500 and prevent the oral interface from being swallowed or dropping out. The other parts of the first variation are the same as the equivalent parts of the second embodiment, thus descriptions of which will not be repeated here. In the first variation, the oral interface device is preferably placed at anterior region (a half or a third) of the tongue and middle region of the upper dental arch. The user's lip can be held between the internal shield member 5010 and external shield member 5012 while the internal shield member 5010 is disposed between the teeth and the lip and the external member 5012 leans against external part of the mouth. The difference between the second variation and the second embodiment of the oral interface device is that the oral interface device has an internal shield member 5014. The other parts of the second variation are the same as the equivalent parts of the second embodiment, thus descriptions of which will not be repeated here. In the second variation, the oral interface device is preferably placed at anterior region (a half or a third) of the tongue and middle region of the upper dental arch. The internal shield member 5014 is disposed between and leans against the teeth and the lip. The internal shield member 5014 can have a larger size that covers either upper and lower teeth or the mouth opening to keep mouth sealed (not shown). The difference between the third variation and the second embodiment of the oral interface device is that the oral interface device has an external shield member 5016. The other parts of the third variation are the same as the equivalent parts of the second embodiment, thus descriptions of which will not be repeated here. In the third variation, the oral interface device is preferably placed at anterior region (a half or a third) of the tongue and middle region of the upper dental arch. The external shield member 5016 leans against external part of the mouth. The external shield member 5016 can have a larger size that covers the mouth opening to keep mouth sealed (not shown).

FIG. 6 shows the fourth variation of an oral interface device according to the second embodiment of the present invention. FIGS. 6A and 6B show the cross-sectional view and the use scenario which the fourth variant of an oral interface device is put into a user's oral cavity with one end connected to a negative pressure source. In the second embodiment, an oral interface 600 comprises a connecting tube 610, with one end connecting to a negative pressure source (not shown); a collapsible chamber 620, with one end connecting to the other end of the connecting tube 610 in relative to the negative pressure source; an open end 640 on another end of the collapsible chamber 620; a non-collapsible structure 630, for example, comprised a plurality of parallel ribs spaced apart, disposed on top internal wall of the collapsible chamber 620, and a first gripping structure 650 and a second gripping structure 650' disposed on top external wall and bottom external wall of the collapsible chamber 620. The first gripping structure 650 and the second gripping structure 650' may comprise several recesses. Referring to FIG. 6B, when the vacuum applied to user's oral cavity, the tongue, soft palate, and other soft tissues are pulled forward to maintain airway patency, and the first gripping structure 650 and the second gripping structure 650' may grip the tongue, hard palate, and other soft tissues to facilitate positioning of the oral interface device 600.

FIG. 7 shows the fifth variation of an oral interface device according to the second embodiment of the present invention. FIGS. 7A and 7B show the cross-sectional view and the use scenario of an oral interface 700 of the fifth variation placing in a user's oral cavity connected to a negative pressure source. The oral interface 700 comprises a connecting tube 710 with one end connecting to a negative pressure source (not shown); a collapsible chamber 720 with one end connecting to the other end of the connecting tube 710 in relative to the negative 10 pressure source; an open end 740 on another end of the collapsible chamber 720; a non-collapsible structure 730, for example, comprised a plurality of parallel ribs spaced apart, disposed on top internal wall of the collapsible chamber 720, and a first gripping structure 750 and a second gripping structure 750' disposed on top external wall and bottom external wall of the collapsible chamber 720. In this manner, the first gripping structure 750 and second gripping structure 750' are disposed on the exterior surface of the top external wall and the exterior surface on the bottom external wall of the collapsible chamber 720, as shown in FIG. 7A. The first gripping structure 750 and the second gripping structure 750' may comprise several protrusions. Referring to FIG. 7B, when the vacuum applied to user's oral cavity, the tongue, soft palate, and other soft tissues are pulled forward to maintain airway patency, and the first gripping structure 750 and the second gripping structure 750' may grip the tongue, hard palate, and other soft tissues to facilitate positioning of the oral interface 700.

FIG. 8 shows the sixth variation of an oral interface device according to the second embodiment of the present invention. FIGS. 8A and 8B show the cross-sectional view and the use scenario of an oral interface of the sixth variation placing in a user's oral cavity connected to a negative pressure source. The oral interface 800 comprises a connecting tube 810, with one end connecting to a negative pressure source (not shown); a collapsible chamber 820, with one end connecting to the other end of the connecting tube 810 in relative to the negative pressure source; an open end 840 on another end of the collapsible chamber 820; a non-collapsible structure 830, for example, comprised of a plurality of parallel ribs spaced apart, disposed on top internal wall of the collapsible chamber 820, and a first gripping structure 850 and a second gripping structure 850' on the top external wall and bottom external wall, respectively, of the collapsible chamber 820. The first gripping structure 850 and the second gripping structure 850' are formed by recesses or sucker shaped concavities on the top external wall and bottom external wall of the collapsible chamber 820. Referring to FIG. 8B, when the vacuum applied to a user's oral cavity, the tongue, soft palate, and other soft tissues are pulled forward to maintain airway patency, and the first gripping structure 850 and the second gripping structure 850' may grip the tongue, hard palate, and other soft tissues to facilitate positioning of the oral interface 800. When oral tissues near the first gripping structure 850 and the second gripping structure 850' moves, the volume of spaces between the tissues and gripping structure 850, 850' may increase, self-generated vacuum effect due to increasing volume increases the forces to pull back the tissue or to prevent the tissue from movement. The oral interface 800 of the present invention could only have a gripping structure 850 disposed on one-side of the external wall of the collapsible chamber 820.

FIG. 9A to FIG. 9J show various steps of a method for using the oral interface 500 according to the second embodiment of the present invention, for an example of methods of using the oral interface devices of the present invention. The methods of using the oral interface device of the present invention are not limited to this. Referring to FIG. 9A, to create vacuum in a user's oral cavity by using the oral interface 500, first place the collapsible chamber 520 of the oral interface 500 into the user's oral cavity. Referring to FIG. 9B, adjust the position of the collapsible chamber 520 on the top of the user's tongue to a proper depth, for example, at about the one third of the total length of the tongue. If the distance from dorsal to tip of tongue is L, the length of the collapsible chamber 520 is preferably ⅓ L, and the collapsible chamber 520 is placed at the anterior surface of tongue within about ⅓ L length from the tip of the tongue. Referring to FIG. 9C, rotate the connecting tube 510 to a suitable orientation by using the collapsible chamber 520 as an axle center, for example, move the connecting tube 510 to the gap between the upper canine and lower canine teeth. Referring to FIG. 9D, let the user bite upper and lower rows of teeth gently. Referring to FIG. 9E, tear the oral strip (560, 562) which comprises an adhesive patch 560 and a covering 562. Referring to FIG. 9F, let the user close lips tightly. Referring to FIG. 9G, apply the adhesive patch 560 on a proper position between the upper and lower lips, for example, applying regions close to the corner of the mouth and above and below the lips in order to restrict the connecting tube 510 at the corner of the mouth and not moving around randomly, or aligning the center of the adhesive patch 560 with the centerline between upper and lower lips. Referring to FIG. 9H, attach the adhesive patch 560 tightly to regions above and below the user's lips to prevent user's mouth from opening involuntarily. Referring to FIG. 9I, connect the oral interface 500 to a negative pressure source (may comprise a liquid storage device 590, a negative pressure connecting tube 592, and a negative pressure generating device 594) and activate the negative pressure source on to create a vacuum in the user's oral cavity. The liquid storage device 590 collects excessive secretions (such as saliva) from user's oral cavity to prevent the negative pressure generation device 594 from contaminated by the secretions. FIG. 9J shows a cross-sectional view of the oral interface 500 connected with the negative pressure source. Under negative pressure environment, the tissues in the oral cavity may lean on the collapsible chamber 520, compress and collapse the collapsible chamber 520. The methods of the present invention employ a non-collapsible structure 530 to support the collapsible chamber 520 in order to maintain fluid passages when the collapsible chamber 520 is collapsed, which keeps the oral cavity in fluid communication with the negative pressure source. The methods of the present invention can further employ a gripping structure 550 on one of the external walls of the collapsible chamber 520. When the collapsible chamber 520 is collapsed in the negative pressure environment, the gripping structure 550 may press up against and grip the soft tissues in the user's oral cavity to facilitate stabilizing of the soft tissue in the oral cavity.

FIG. 10 shows an oral interface device according to the third embodiment of the present invention. FIG. 10A to FIG. 10C show perspective, side and top views of the third embodiment, respectively. According to the third embodiment, an oral interface 1000 comprises a connecting tube 1010 with one end 1015 connecting to a negative pressure source (not shown), a collapsible chamber 1020 with one end connecting to the other end of the connecting tube 1010 in relative to the negative pressure source, an open end 1040 on another end of the collapsible chamber 1020, a non-collapsible structure 1030, 1030' on the two opposite internal walls of the collapsible chamber 1020, a first gripping structure 1050 and a second gripping structure 1050' on two opposite external walls of the collapsible chamber 1020, an internal shield member 1060 and the external shield member 1070 disposed between the collapsible chamber 1000 and connecting tube 1010. The non-collapsible structure 1030, 1030' is the same as the non-collapsible structure 430, 430' in FIG. 4, which comprises a plurality of first ribs 1030 and a plurality of second ribs 1030'. Each individual of the first ribs 1030 can be parallel to each other and spaced apart on an internal wall of the collapsible chamber 1020. Each individual of the second ribs 1030' can be parallel to each other and spaced apart on another internal wall of the collapsible chamber 1020. Besides, the first ribs 1030 and the second ribs 1030' can have a perpendicular or non-parallel stack configuration. The first gripping structure 1050 may comprise a plurality of recesses on the top external wall of the collapsible chamber 1020, and the second gripping structure 1050' may comprise a plurality of recesses on the bottom external wall of the collapsible chamber 1020.

FIG. 11A to FIG. 11E shows application diagrams and method of applying the oral interface 1000 of the third embodiment of the present invention. FIG. 11A is a front view showing the first step of the method to place the collapsible chamber 1020 of the oral interface 1000 on a half or a third anterior portion of the tongue and middle region of the upper dental arch. The connecting tube 1010 is moved to the gap at the occlusive place of the upper and lower canine teeth. FIG. 11B is a cross-sectional view which illustrates a present method to place the internal shield member 1060 of oral interface 1000 between the teeth and the lips and to place the external shield member 1070 outside of mouth. The internal and external shield member, 1060 and 1070, jointly clamp tissues around a user's lips and facilitate securing the oral interface 1000. FIG. 11C is a front view which presents the current method by positioning the oral interface 1000 and then connecting negative pressure source (the liquid storage device 1080, negative pressure connecting tube 1082, the negative pressure generating device 1084). The liquid storage device 1080 collects excess secretions (such as saliva) from the oral cavity and prevents the secretions contaminate the negative pressure generating device 1084. FIG. 11D is a cross-sectional view which illustrates a current method using the oral interface 1000 to create a negative pressure environment in the oral cavity of a user by the means of using the negative pressure source (1080, 1082, 1084). Under this negative pressure environment, the tissues in the oral cavity may lean against, compress and collapse the collapsible chamber 1020. The first gripping structure 1050 and the second gripping structure 1050' may grip the soft tissues in the oral cavity of a user and facilitate stabilizing the soft tissues in the oral cavity. FIG. 11E is a front view which shows the current method to attach the adhesive patch 1090 on the lips corner of a user after placing the oral interface 1000 in the oral cavity of a user, in order to prevent a user from opening involuntarily.

FIG. 12A to FIG. 12C show perspective views of variations of the oral interface 1000 according to the third embodiment of the present invention. FIG. 13A to FIG. 13C show front views of these variations in using status. FIG. 12A is the first variation of the oral interface 1000. The difference from the oral interface 1000 is that the first variation uses an adhesive patch 1091 and an external fixing part 1071 to replace the combination of internal shield member 1060 and the external shield member 1070. The other parts of the first variation are the same as the equivalent parts of the third embodiment. The external fixing part 1071 is connected to the connecting tube 1010. The adhesive patch 1091 can cover the extension member 1071a of the external fixing part 1071 and then attach to regions above and below the lips. Therefore, the oral interface device of the first variation can be restricted within a fixed position (such as the corner of the mouth). FIG. 12B shows the second variation of the oral interface 1000. The difference between oral interface 1000 and the second variation is that the second variation uses an adhesive patch 1092 and an external fixing part 1072 to replace the combination of internal shield member 1060 and the external shield member 1070. The other parts of the first variation are the same as the equivalent parts of the oral interface 1000. The external fixing part 1072 is attached to the connecting tube 1010. One edge of the adhesive patch 1092 has a circular notch 1092a. Preferably, the size of circular notch 1092a is larger or equal to the external size (like the external diameter) of the connecting tube 1010 but smaller than an external size of the external fixing part 1072. The circular notch 1092a encircles around the periphery of the connecting tube 1010 between the lips and the external fixing part 1072. The adhesive patch 1092 attaches to regions above and below the lips. When the second variation of the oral interface device is placed in the oral cavity of a user, the adhesive patch 1092 can restrict the connecting tube 1010 from moving, as shown in FIG. 13B. FIG. 12C shows the third variation of the oral interface 1000. The difference between the oral interface 1000 and the second variation is that the second variation uses an adhesive patch 1093 and an internal shield member 1063 to replace the combination of internal shield member 1060 and the external shield member 1070. The other parts of the first variation are the same as the equivalent parts of the oral interface 1000. The internal shield member 1063 situates between the teeth and the lips of a user. One edge of the adhesive patch 1093 has a circular notch 1093a. Preferably, the size of circular notch 1093a is larger or equal to the external size (like the external diameter). The circular notch 1093a encircles around the periphery of the connecting tube 1010. The adhesive patch 1093 attaches to regions above and below the lips. When the third variation of the oral interface device is placed in the oral cavity of a user, the adhesive patch 1093 can prevent the connecting tube 1010 from moving, as shown in FIG. 13C.

FIG. 14A show an oral interface device according to the fourth embodiment of the present invention. According to the fourth embodiment, an oral interface 1400 of the present invention comprises a connecting tube 1410 with one end in fluid communication with a negative pressure source (not shown), a collapsible chamber 1420 with one end in fluid communication with the other end of the connecting tube 1410 in relative to the negative pressure source, an open end 1440 on the other end of the collapsible chamber 1420, a non-collapsible structure 1430, for example, comprising at least a rib disposed on at least one internal wall of the collapsible chamber 1420, an internal shield member 1460 formed at the open end 1440 on the collapsible chamber 1420. When the oral interface 1400 is placed in a user's oral cavity, the collapsible chamber 1420 is placed between upper lip and lower lip, and the external width (not shown) of the collapsible chamber 1420 is smaller than the width of the user's mouth, and is preferably smaller than one half of the width of the user's mouth. The internal shield member 1460 is situated between the user's teeth and lips. FIG. 14B shows an oral interface device according to the fifth embodiment of the present invention. According to the fifth embodiment, an oral interface 1401 of the present invention comprises a connecting tube 1411 with one end connecting to a negative pressure source (not shown); a collapsible chamber 1421 with one end connecting to the other end of the connecting tube 1411 in relative to the negative pressure source, an open end 1441 on another end of the collapsible chamber 1421, a non-collapsible structure 1431, for example, comprising of at least a rib disposed on at least one internal wall of the collapsible chamber 1421, and an external shield member 1470 disposed between the collapsible chamber 1421 and the connecting tube 1411. When the oral interface 1401 is applied in a user's oral cavity, the collapsible chamber 1421 is placed between the user's upper lip and lower lip, and the external shield member 1470 leans on the outside surface of the user's mouth. FIG. 14C shows an oral interface device according to the sixth embodiment of the present invention. According to the sixth embodiment, an oral interface 1402 of the present invention comprises a connecting tube 1412 with one end connecting to a negative pressure source (not shown); a collapsible chamber 1422 with one end connecting to the other end of the connecting tube 1412 in relative to the negative pressure source, an open end 1442 on another end of the collapsible chamber 1422, a non-collapsible structure 1432, for example, comprising of at least a rib disposed on at least one internal wall of the collapsible chamber 1422, an internal shield member 1462 disposed at the open end 1442 on the collapsible chamber 1422, and an external shield member 1472 disposed between the collapsible chamber 1422 and the connecting tube 1412. When the oral interface 1402 is applied in a user's oral cavity, the internal shield member 1462 and the external shield member 1472 may clamp the user's upper and lower lips together, and the collapsible chamber 1422 is placed between the user's upper lip and lower lip.

FIG. 15 and FIG. 16 show the first and second variations of the oral interface 1400 according to the fourth embodiment of the present invention. FIGS. 15A to 15D are perspective, top, side, and front views of the first variation, respectively. In the first variation, an oral interface 1500 of the present invention comprises a connecting tube 1510 with one end in fluid communication with a negative pressure source (not shown), a collapsible chamber 1520 with one end in fluid communication with the other end of the connecting tube 1510 in relative to the negative pressure source, an open end 1540 on the other end of the collapsible chamber 1520, a non-collapsible structure comprising a plurality of first ribs 1530 and a plurality of second ribs 1530'. Each individual of the first ribs 1530 can be parallel to each other and spaced apart on an internal wall of the collapsible chamber 1520. Each individual of the second ribs 1530' can be parallel to each other and spaced apart on another internal wall of the collapsible chamber 1520. Besides, the first ribs 1530 and the second ribs 1530' can have a perpendicular stack configuration. An internal shield member 1560 is disposed between the collapsible chamber 1520 and the open end 1540. When placing the oral interface device in a user's oral cavity, the internal shield member is situated between the teeth and the lips of the user. FIG. 15 shows a top view of the second variation. The difference between the first variation and the second variation is that internal shield member 1561 of the oral interface 1501 has a gripping structure comprising of a single or plural recesses 1551 on one surface facing the user's teeth. When applying the oral interface device with negative pressure source to create a negative pressure environment in the user's oral cavity, the recesses 1551 can grip the teeth or surrounding soft tissues to facilitate positioning of the collapsible chamber 1521. The recesses 1551 may also enhance distribution of negative pressure to the oral cavity. The other parts of the oral interface 1501, such as a connecting tube 1511, a collapsible chamber 1521 with an open end 1541, and non-collapsible structure (1531, 1531'), are the same as the equivalent parts of the first variation, thus descriptions of which will not be repeated here.

FIG. 17A and FIG. 17B show the first variation of the oral interface 1402 according to the sixth embodiment of the present invention. The difference between the oral interface 1700 of the first variation and the oral interface 1402 is that the external shield member comprises reclosable fasteners (such as dual lock tape) 1780, 1780' and a shield member 1770. When using the oral interface 1700, one side of the reclosable fasteners 1780 and 1780' are attached to regions above and below the user's lips and the shield member 1770 is attached to the other side of the reclosable fasteners 1780, 1780' and leans against the outside surface of the user's mouth. The other parts of the oral interface 1700, such as a connecting tube 1710, a collapsible chamber 1720 with an open end 1740, a non-collapsible structure 1730 and the internal shield member, are the same as the equivalent parts of the oral interface 1402, thus descriptions of which will not be repeated here.

FIG. 17C to FIG. 17F show the second to fifth variations of the sixth embodiment of the present invention, respectively. The difference of these variations with the oral interface 1402 is the structure of the external shield members, the other parts of the variations are the same as the equivalent parts of the oral interface 1402, but not limit to it, for example, the non-collapsible structure of these variations can apply other types and shapes of above-mentioned embodiments, and these variations can also use other gripping structure described in the above-mentioned embodiments. In the second variation, the external shield member comprises reclosable fasteners 1780, 1780' and a movable external shield 1771 which is cross-shaped and assembled with the collapsible chamber 1720. In a use scenario of the oral interface 1700, one side of the reclosable fasteners 1780, 1780' are attached to regions above and below the user's lips and the shield member 1771 is attached to the other side of the reclosable fasteners 1780, 1780' to facilitate closing of the user's mouth. The shield member 1771 can also temporarily detach from the reclosable fasteners 1780, 1780' to allow the user to open mouth freely. In the third to fifth variations, the external shield members comprise reclosable fasteners 1780, 1780' and movable external shields 1772, 1773, or 1774, respectively with different shapes. In a use scenario of the oral interface 1700, one side of the reclosable fasteners 1780, 1780' are attached to regions above and below the user's lips and the shield members 1772, 1773, or 1774 are attached to the other side of the reclosable fasteners 1780, 1780' to facilitate closing of the user's mouth. The shield members 1772, 1773, or 1774 can also temporarily detach from the reclosable fasteners 1780, 1780' to allow the user to open mouth freely.

FIG. 18 shows a side view of an oral interface device according to the seventh embodiment. According to the seventh embodiment of the present invention, an oral interface 1800 comprises a connecting tube 1810 with one end in fluid communication with a negative pressure source (not shown), a collapsible chamber 1820 with one end in fluid communication with the other end of the connecting tube 1810 in relative to the negative pressure source, an open end 1840 on the other end of the collapsible chamber 1820, a non-collapsible structure 1830, for example, comprising at least a rib disposed on at least one internal walls of the collapsible chamber 1820, an internal shield member at the open end 1840 of the collapsible chamber 1820, and a first gripping structure and a second gripping structure. The first and second gripping structures comprise a plurality of protrusions 1850, 1850' at the top and bottom external walls of the collapsible chamber 1820, respectively. When the oral interface device is placed in a user's oral cavity, the internal shield member 1860 stays in between the teeth and the lips of the user. When a negative pressure environment is created in the user's oral cavity, the first and the second gripping structures can grip the user's upper and lower lips.

FIG. 19A shows an oral interface device and method according to the eighth embodiment of the present invention. According to the eighth embodiment, an oral interface 1900 comprises a connecting tube 1910 with one end in fluid communication with a negative pressure source (not shown), a collapsible chamber 1920 with one end in fluid communication with the other end of the connecting tube 1910 in relative to the negative pressure source, an open end 1940 on the other end of the collapsible chamber 1920, a first griping structure and a second gripping structure formed by a plurality of protrusions 1950 and 1950' on top and bottom external walls of the collapsible chamber 1902, respectively, an internal shield member 1960 disposed at the open end 1940, a movable external shield member 1970 disposed at the connecting end between the collapsible chamber 1920 and the connecting channel 1910. When placing the oral interface 1900 in a user's oral cavity, the internal shield member 1960 is placed between the teeth and lips of the user. The movable external shield member 1970 has a through hole in the center and can slip on the outside shell of the collapsible chamber 1920 and can interlock with the first griping and the second gripping structures 1950, 1950'. The movable external shield member 1970 can lean against the outside surface of the mouth and clamp the user's lips in with the internal shield member 1960. FIG. 19B shows that the movable external shield member 1970 can move forward and backward on the outer shell of the collapsible chamber 1920, in order to interlock with different protrusions 1950, 1950' of the first gripping structure and the second gripping structure and adjust tightness of clamping the user's lips.

FIG. 20A to FIG. 20D show the first to fourth variations of the eighth embodiment of the present invention, respectively. The difference of these variations with the oral interface 1900 according to the eighth embodiment is the structure of the movable external shield members, the other parts of the variations are the same as the equivalent parts of the oral interface 1900. The first variation has a movable external shield member 1971 which is a cross-shaped patch assembled with the collapsible chamber 1920. In a use scenario of the oral interface 1900, the movable external shield member 1971 can slip and move forward and backward on the outer shell of the collapsible chamber 1920, in order to interlock with different protrusions 1950 and adjust tightness of clamping the user's lips. The second to fourth variations have movable external shield members 1972, 1973, and 1974 with other different shaped patch assembled with the collapsible chamber 1920. In a use scenario of the oral interface 1900, the movable external shield members 1972, 1973, and 1974 can slip and move forward and backward on the outer shell of the collapsible chamber 1920, in order to interlock with different protrusions 1950 and adjust tightness of clamping the user's lips.

FIG. 21 shows an oral interface device and method according to the ninth embodiment of the present invention. FIG. 21A to 21C show the partial cross-sectional, cross-sectional, and front views, respectively. According to the ninth embodiment of the present invention, the oral interface 2100 comprises a connecting tube 2110 with one end in fluid communication with the negative pressure source (not shown), a collapsible chamber 2120 with one end in fluid communication with the other end of the connecting tube 2110 in relative to the negative pressure source, an open end 2140 on the other end of the collapsible chamber 2110, a non-collapsible structure 2130 comprising, for example, a rib disposed on at least one internal wall of the collapsible chamber 2120, an internal shield member 2160 formed at the open end 2140 of the collapsible chamber 2120, and an external shield member composed of reclosable fasteners (such as dual lock tape) 2180, 2180' and an oral mask 2170. The oral mask 2170 has two openings and contains absorbent 2190 internally. One openings of the oral mask is in fluid communication with the other end of the connecting tube 2110 in relative to the collapsible chamber 2120, and the other opening of the oral mask 2170 is in fluid communication with a negative pressure source 2111. The internal space of the oral mask 2170 allows fluid to pass through and the absorbent 2190 can contain absorb liquid from the connecting tube 2110. The oral mask 2170 can have a pair of ear loops 2171. In a use scenario of the oral interface 2100, the oral interface 2100 is placed in the anterior portion of the oral cavity of a user. The internal shield member 2160 is placed between the teeth and the lips. The reclosable fasteners (such as dual lock tape) 2180, 2180' have one side attached to regions above and below the lips. The mask 2170 has one side with dual lock's surface characteristics and can be attached to another side of the reclosable fasteners (such as dual lock tape) 2180, 2180. The pair of the ear loops 2172 of the oral mask 2171 can be hooked on the user's ears to facilitate fixing the oral mask 2170. When applying negative pressure to generate a negative pressure environment in a user's cavity, liquid secreted from the user's oral cavity flows through the connecting tube 2110 and then is absorbed by the absorbent 2190 of the oral mask 2170 without entering the negative pressure source 2112.

Figure 22C:
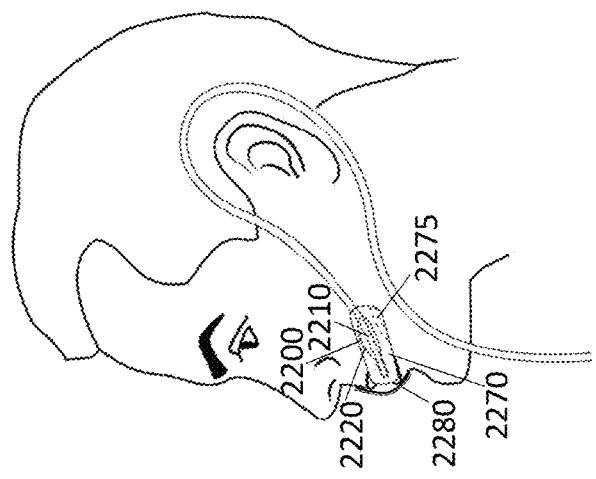
FIG. 22C illustrates another placement condition of the oral interface.
Figure 22B:
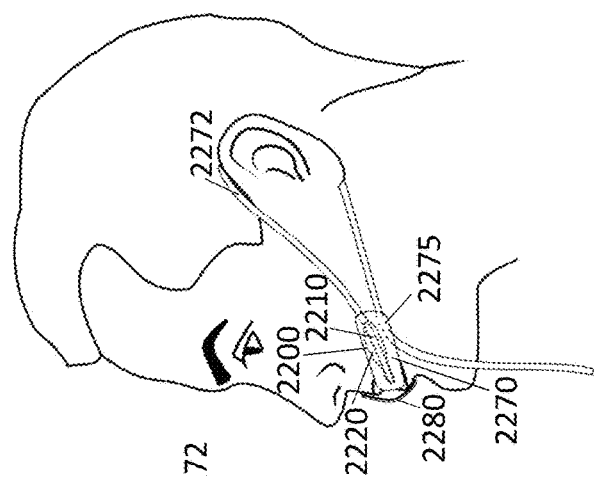
FIG. 22A and FIG. 22B illustrates front and side views of an oral interface in placement according to a tenth embodiment of the present invention.
Figure 22A:
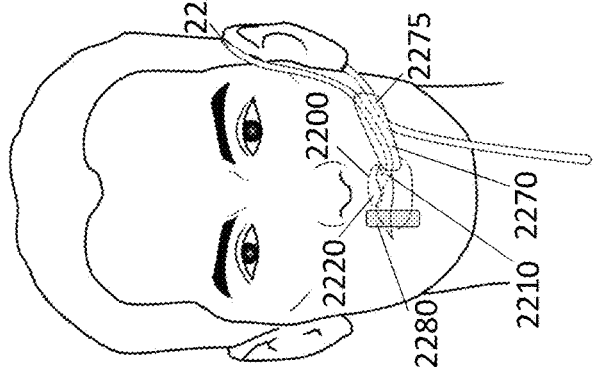

FIG. 22 shows an oral interface device and method according to the tenth embodiment of the present invention. FIG. 22A to 22B show front and side views in a use scenario of the tenth embodiment. FIG. 22C shows another use scenario. According to the tenth embodiment of the present invention, an oral interface 2200 comprises a connecting tube 2210, a collapsible chamber 2220, a non-collapsible structure (not shown), an external shield member 2270, and an adhesive patch. The connecting tube 2210 has one end connecting to the collapsible chamber 2220. The connecting tube 2210 extends and passes through inside of the external shield member 2270 and forms a curved portion outside of the external shield member 2270, and passes through again and is fixed at the tube slot structure 2275, and then connects the connecting tube's the other end to the negative pressure source (not shown). The curved portion of the connecting tube 2210 forms an ear loop 2272. In a use scenario of the oral interface 2200, the ear loop 2272 formed by the curved portion of the connecting tube 2210 hooks on a user's ear and the adhesive patch 2280 attached to the user's lips near the corner of the mouth. The connecting tube 2210 can slide in the tube slot structure 2275 to adjust size of the ear look 2272, in order to fit different users' size or wear tightness. Besides, the collapsible chamber 2220 of the oral interface 2200 and the non-collapsible structure can apply above-mentioned other embodiments and their variations, thus descriptions of which will not be repeated here. FIG. 22C shows another use scenario of the oral interface 2200. The connecting tube 2210 extends and passes through inside of the external shield member 2270, and it does not passes through the external shield member 2270 again and fixes on the tube slot structure 2275 but connects is the other end directly to the negative pressure source. The adhesive patch 2280 is attached to the user's lips near the corner of the mouth.

Figures 23A, 23B, 23C:
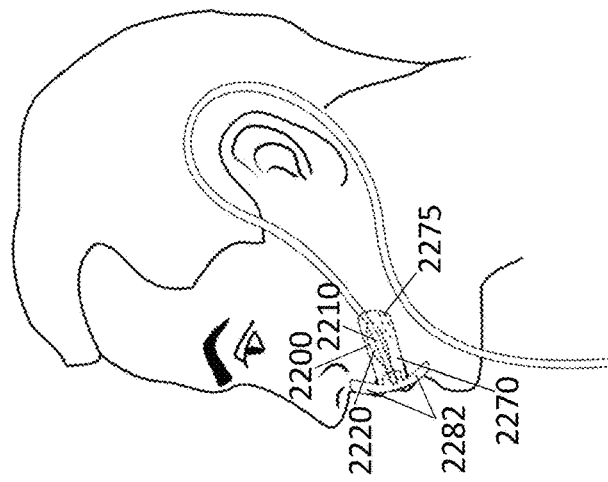
FIG. 23A and FIG. 23B illustrates front and side views of a variation of the oral interface according to the tenth embodiment of the present invention.
FIG. 23C illustrates another placement condition of the oral interface.

FIG. 23 shows a variation of the tenth embodiment of the present invention. FIG. 23A to 23B show the front and side views in a use scenario of the variation. FIG. 22C shows another use scenario. The difference between the variation and the tenth embodiment is that a T-shaped lip guard 2282 replaces the adhesive patch 2280, and the other parts of the variation are the same as the equivalent parts of the tenth embodiment. The lip guard 2282 has one end connected to the external shield member 2270, and the connecting tube 2210 extends and passes through inside of the external shield member 2270 and forms a curved portion outside of the external shield member 2270, and passes through again and is fixed at the tube slot structure 2275, and then connects the connecting tube's the other end to the negative pressure source (not shown). The curved portion of the connecting tube 2210 forms an ear loop 2272. In a use scenario of the oral interface 2200, the ear loop 2272 formed by the curved portion of the connecting tube 2210 hooks on a user's ear and the lip guard 2282 leans on the user's lips. FIG. 23C shows another use scenario of the oral interface 2200. The connecting tube 2210 extends and passes through inside of the external shield member 2270, and it does not passes through the external shield member 2270 again and fixes on the tube slot structure 2275 but connects is the other end directly to the negative pressure source. The lip guard 2282 leans on the user's lips near the corner of the mouth.

The oral interface and methods of the present invention may further be placed at other proper location in the oral cavity, for example, between the tongue and the hard palate, between the tongue and the lower jaw (under the tongue), between the teeth and the front internal wall of the oral cavity (the upper and lower lips), between the teeth and the side walls of the oral cavity (internal walls of the cheek), or between the tongue and the soft palate. The oral interface devices and methods of the present invention may further be used in combination with other apparatus for the treatment of sleep-disordered breathing. For example, the oral interface devices of the present invention can be in combination with one-way nasal valve devices, such as those described in, for example, U.S. Pat. No. 8,061,357. By increasing airway pressure using such nasal valve devices while preventing mouth leakage in the oral cavity by using the present invention, the pressure gradient from airway to the oral cavity can be increased and maintained, thus urging the soft palate toward the oral cavity and the tongue toward the upper hard palate to clear upper airway.

The oral interface devices and methods of the present invention may further be used in combination with a conventional constant positive airway pressure (CPAP) apparatus for delivering air under positive pressure to the nasal airway. With the device of the present invention keeping mouth closing and preventing air leakage in the oral cavity, and the CPAP apparatus increasing pressure in the airway, the pressure gradient between the airway and the oral cavity can be increased and maintained, thus urging the soft palate toward the oral cavity and the tongue toward the upper hard palate to clear upper airway. Meanwhile, using the negative pressure oral interface device of the present invention, the setting pressure of the CPAP can be reduced, or furthermore the positive airway pressure treatment can periodically stop/activate or decrease/increase the positive pressure, in order to reduce the uncomfortableness of breathing caused by continuous positive pressure and increase patient compliance.

The oral interface devices and methods of the present invention may further be used in combination with other oral appliance. The oral appliance can adjust biting position of upper and lower jaws and move the lower jaw forward to increase airway space near back of the throat. With the device of the present invention to provide negative pressure, keep the mouth closed and prevent air leakage in the oral cavity, the pressure gradient between the airway and the oral cavity can be increased and maintained, thus urging the soft palate toward the oral cavity and the tongue toward the upper hard palate to clear upper airway.

The oral interface devices and methods of the present invention may further be used in combination with other breathing detection device. The breathing detection device can detect breathing flow rate, and the negative pressure delivered by the present oral interface device can be activated or increased when apnea or hypopnea events are detected. Thus the operating time of the negative pressure source can be reduced and energy-saving and quiet operation can be achieved.

The foregoing is only specific embodiments of the invention only and not intended to limit the scope of the invention patent; where others without departing from the spirit of the invention disclosed under the equivalent of completion of the change or modification, the following should be included in the patent scope.

What is claimed is:

1. An oral interface, comprising:
a connecting tube having opposite first and second longitudinal ends, wherein the first end is configured to be in fluid communication with a negative pressure source;
a collapsible chamber having upper and lower walls and first and second open longitudinal ends, the upper and lower walls each having an exterior surface and an interior surface, wherein the first longitudinal end of the collapsible chamber is fluidly connected to the second longitudinal end of the connecting tube; and
two non-collapsible structures disposed between the interior surface of the upper wall of the collapsible chamber and the interior surface of the lower wall of the collapsible chamber, wherein the two non-collapsible structures having lengths extending longitudinally along the collapsible chamber, wherein the two non-collapsible structures are spaced apart from one another such that the interior surfaces of the upper and lower walls of the collapsible chamber and the two non-collapsible structures define a fluid channel extending longitudinally along the collapsible chamber and fluidly connecting the second open longitudinal end of the collapsible chamber and the second longitudinal end of the connecting tube.

2. The oral interface of claim 1, wherein the two non-collapsible structures comprise two first ribs.

3. The oral interface of claim 2, further comprising a plurality of second ribs disposed between the upper and lower walls of the collapsible chamber, the two first ribs and the plurality of second ribs constitute a perpendicular or non-parallel stack configuration.

4. The oral interface of claim 1, wherein the two non-collapsible structures are spaced longitudinally inward from the second open longitudinal end of the collapsible chamber.

5. The oral interface of claim 4, wherein the two non-collapsible structures are spaced longitudinally inward from the first open longitudinal end of the collapsible chamber.

6. The oral interface of claim 1, wherein the collapsible chamber has a first gripping structure and/or a second gripping structure disposed on the exterior surface of the upper wall and/or the exterior surface of the lower wall of the collapsible chamber, the first gripping structure and/or the second gripping structure configured to grip soft tissues of the oral cavity to facilitate positioning of the oral interface.

7. The oral interface of claim 6, wherein the first gripping structure and/or the second gripping structure comprise one or a plurality of the following member: recesses, protrusions and sucker shaped concavities on the exterior surface of the upper wall and/or the exterior surface of the lower wall of the collapsible chamber.

8. The oral interface of claim 1, further comprising an internal shield member disposed between the collapsible chamber and the connecting tube, the internal shield member being adapted to be placed between teeth and lips when the oral interface is placed in a user's oral cavity.

9. The oral interface of claim 1, further comprising an external shield member disposed between the collapsible chamber and the connecting tube, the external shield member being adapted to be leaned against outside of mouth when the oral interface is placed in a user's oral cavity.

10. The oral interface of claim 1, further comprising an internal shield member and an external shield member disposed between the collapsible chamber and the connecting tube, wherein when the oral interface is placed in a user's oral cavity, the internal shield member and the external shield member are adapted to jointly clamp the user's lips, the internal shield member is adapted to be placed between the user's lips and teeth, and the external shield member is adapted to be leaned against outside of mouth.

11. The oral interface of claim 1, further comprising an adhesive patch adapted to be adhered to a predetermined location at an outside surface of mouth.

12. The oral interface of claim 1, wherein the two non-collapsible structures are parallel to one another.

13. The oral interface of claim 1, wherein the two non-collapsible structures are disposed inward of side edges of the upper and lower walls of the collapsible chamber.

14. The oral interface of claim 1, wherein the two non-collapsible structures are mounted to the interior surface of the upper wall of the collapsible chamber and extend toward the interior surface of the lower wall.

15. The oral interface of claim 1, wherein the two non-collapsible structures are mounted to the interior surface of the lower wall of the collapsible chamber and extend toward the interior surface of the upper wall.

16. The oral interface of claim 1, wherein the two non-collapsible structures are disposed entirely between the interior surfaces of the upper and lower walls of the collapsible chamber.

* * * * *